United States Patent
Sagel et al.

(10) Patent No.: US 10,849,729 B2
(45) Date of Patent: *Dec. 1, 2020

(54) MULTI-PHASE ORAL CARE COMPOSITIONS

(71) Applicant: The Procter & Gamble Company, Cincinnati, OH (US)

(72) Inventors: Paul Albert Sagel, Mainville, OH (US); Jayanth Rajaiah, Loveland, OH (US); Michael David Curtis, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 16/842,799

(22) Filed: Apr. 8, 2020

(65) Prior Publication Data
US 2020/0330206 A1 Oct. 22, 2020

Related U.S. Application Data

(60) Provisional application No. 62/834,647, filed on Apr. 16, 2019.

(51) Int. Cl.
*A61C 19/06* (2006.01)
*A61Q 11/00* (2006.01)
(Continued)

(52) U.S. Cl.
CPC .............. *A61C 19/066* (2013.01); *A61K 8/21* (2013.01); *A61K 8/22* (2013.01); *A61K 8/42* (2013.01);
(Continued)

(58) Field of Classification Search
None
See application file for complete search history.

(56) References Cited

U.S. PATENT DOCUMENTS 5,077,047 A * 12/1991 Biss .................. A61K 8/02
424/405
5,674,436 A * 10/1997 Breitenbach ............. C08K 3/20
264/12
(Continued)

FOREIGN PATENT DOCUMENTS

EP 1696866 B1 * 10/2013 ............. A61Q 11/00
EP 3315117 A1 10/2016
(Continued)

OTHER PUBLICATIONS

"Brush & Bleach Teeth Whitening Kit" Anonymous Database GNPD MINTEL; Feb. 22, 2018, retrieved from www.gnpd.com abstract.
(Continued)

*Primary Examiner* — Isaac Shomer
(74) *Attorney, Agent, or Firm* — Parker D. McCrary

(57) ABSTRACT

Multi-phase oral care compositions for whitening teeth, including hydrophilic bleaching agent particles in a hydrophobic phase with a melting point of from about 40° C. to about 80° C. The hydrophilic bleaching agent particles can include peroxide compounds and/or hydrogen peroxide adducts. The hydrophilic bleaching agent particle can have a solubility in water of at least about 20 parts, by weight of the particles, in about 100 parts, by weight of water.

32 Claims, 2 Drawing Sheets

(51) Int. Cl.
  *A61K 8/22* (2006.01)
  *A61K 8/92* (2006.01)
  *A61K 8/42* (2006.01)
  *A61K 8/21* (2006.01)
  *A61K 8/81* (2006.01)

(52) U.S. Cl.
  CPC .......... *A61K 8/8111* (2013.01); *A61K 8/8176* (2013.01); *A61K 8/92* (2013.01); *A61Q 11/00* (2013.01); *A61K 2800/81* (2013.01); *A61K 2800/87* (2013.01); *A61K 2800/88* (2013.01); *A61K 2800/92* (2013.01)

(56) References Cited

U.S. PATENT DOCUMENTS

| | | | |
|---|---|---|---|
| 6,343,933 B1* | 2/2002 | Montgomery | A61C 19/066 433/216 |
| 8,623,388 B2 | 1/2014 | Rajaiah | |
| 2004/0105823 A1 | 6/2004 | Kamasaka | |
| 2005/0008584 A1* | 1/2005 | Montgomery | A61K 8/927 424/53 |
| 2005/0036958 A1 | 2/2005 | Feng | |
| 2005/0137109 A1 | 6/2005 | Quan et al. | |
| 2008/0274067 A1 | 11/2008 | Chaffer | |
| 2009/0238776 A1 | 9/2009 | Baig | |
| 2012/0301522 A1* | 11/2012 | Prosise | A61K 8/0241 424/401 |
| 2015/0366778 A1 | 8/2015 | Boyd | |
| 2017/0172864 A1 | 6/2017 | Evans | |
| 2018/0133119 A1 | 5/2018 | Rajaiah | |
| 2018/0133120 A1 | 5/2018 | Rajaiah | |
| 2018/0133121 A1 | 5/2018 | Rajaiah | |
| 2018/0133123 A1 | 5/2018 | Rajaiah | |
| 2018/0133128 A1 | 5/2018 | Rajaiah | |
| 2018/0133502 A1 | 5/2018 | Rajaiah | |
| 2018/0140516 A1 | 5/2018 | Rajaiah | |
| 2018/0168993 A1 | 6/2018 | Yuan | |
| 2018/0243178 A1 | 8/2018 | Nesta | |
| 2019/0054003 A1 | 2/2019 | Evans | |

FOREIGN PATENT DOCUMENTS

| | | |
|---|---|---|
| EP | 3315118 A1 | 10/2016 |
| EP | 3315119 A1 | 10/2016 |
| EP | 3315171 A1 | 10/2016 |
| EP | 3315172 A1 | 10/2016 |
| EP | 3315173 A1 | 10/2016 |
| WO | WO2006138550 A1 | 12/2006 |
| WO | WO2013095369 A2 | 12/2011 |
| WO | WO2017106588 A1 | 12/2016 |
| WO | W02018081004 A3 | 10/2017 |
| WO | WO2018081001 A1 | 10/2017 |

OTHER PUBLICATIONS

"Extreme White Fresh Mint Whitening Toothpaste" Anonymouse, Database GNPD MINTEL, Nov. 15, 2018; from retrieved www.gnpd.com—abstract.
EP Search Report CM5055F for 19169614.5-1114 dated Oct. 28, 2019.
EP Search Report CM5056F for 19169615.2-1114 dated Oct. 28, 2019.
EP Search Report CM5057F for 19169621.0-1114 dated Jul. 17, 2019.
EP Search Report CM5059F for 19169629.3-1114 dated Nov. 11, 2019.
EP Search Report CM5060F for 19169630.1-1114 dated Jul. 17, 2019.
EP Search Report CM5061F for 19169637.6-1114 dated Nov. 11, 2019.
EP Search Report for CM5058F—19169624.4-1114 dated Nov. 11, 2019.
Solvay Brochure IXPER(R) C calcium peroxide. www.solvay.com, May 22, 2020.
EP Search Report for CM5061M2—Application No. 20168620.1-1112 dated Jul. 16, 2020.
U.S. Appl. No. 16/842,797, filed Apr. 16, 2020, Sagel et al.
U.S. Appl. No. 16/842,798, filed Apr. 16, 2020, Sagel et al.
U.S. Appl. No. 16/842,800, filed Apr. 16, 2020, Sagel et al.
U.S. Appl. No. 16/842,802, filed Apr. 16, 2020, Sagel et al.
U.S. Appl. No. 16/842,804, filed Apr. 16, 2020, Sagel et al.
U.S. Appl. No. 16/842,806, filed Apr. 16, 2020, Sagel et al.
EP Search Report CM5061M and Wrriten Opinion for APplication No. 20168616.9-1112 dated Aug. 3, 2020.

* cited by examiner

MULTI-PHASE ORAL CARE COMPOSITIONS

FIELD OF THE INVENTION

The present invention relates to multi-phase oral care compositions comprising bleaching agents.

BACKGROUND OF THE INVENTION

Currently in the marketplace are dental products by which various cosmetic and/or therapeutic actives are delivered to teeth and the oral cavity. Examples of such products include: brushing aids, such as dentifrice products for delivery of oral care actives for example polyphosphates or fluorides; mouthwashes containing breath fresheners or antibacterial actives; and whitening strips for the delivery of bleaching actives to the teeth. In particular, the use of a dental strip has been recognized as a convenient and inexpensive way to deliver cosmetic and therapeutic benefits to the teeth and mucosal surfaces of the oral cavity; for example, dental whitening strips, where a whitening composition is applied to a strip and thereafter applied to the teeth to achieve sustained contact between the teeth and the whitening composition.

Despite the above known approaches for the treatment of oral conditions, especially for the whitening of teeth, a need still exists for providing products with both improved bleaching efficacy, increased speed of whitening, decreased tooth-sensitivity, and/or decreased oral soft tissue irritation. The prior art has generally attempted to address improved bleaching efficacy and/or increased speed of whitening by increasing the level of the bleaching agent in the compositions. This approach, however, presents several problems. First the participant may experience increased irritation and/or sensitivity which may be associated with using an increased amount of a bleaching agent. Furthermore, some regulatory authorities and legislation in various geographies throughout the world do not allow bleaching agents to be used in products at levels above certain concentrations. Therefore, despite the above known approaches for the treatment of oral conditions, especially for the whitening of teeth, a need still exists for providing products with improved bleaching efficacy, increased speed of whitening, decreased tooth-sensitivity, and/or decreased oral soft tissue irritation. The present invention overcomes some of the limitations of the prior art, and relates to a multi-phase oral composition comprising hydrophilic bleaching agent particles and a hydrophobic phase, wherein in certain embodiments the hydrophobic phase may be in predominant proportion relative to the hydrophilic bleaching agent particles.

SUMMARY OF THE INVENTION

A multi-phase oral composition is provided that comprises from about 0.01% to about 40% by weight of the multi-phase oral composition of hydrophilic bleaching agent particles; at least about 60% by weight of the multi-phase oral composition of a hydrophobic phase; and wherein at least about 20 parts by weight of the hydrophilic bleaching agent particles are soluble in about 100 parts by weight of water, or the hydrophilic bleaching agent particles swells by at least about 20% upon contact with water.

A multi-phase oral care composition comprising solid hydrophilic bleaching agent particles; and at least about 50%, by weight of the dispersion, of hydrophobic phase, wherein the multi-phase oral care composition has a drop melting point of from about 40° C. to about 80° C.

A semisolid oral dispersion comprising solid hydrophilic bleaching agent particles; and at least about 50%, by weight of the dispersion, of hydrophobic phase.

The present invention may be used to deliver whitening benefits to the oral cavity by directly applying the composition to the teeth. In addition, the composition may be applied via a delivery carrier, such as a strip or film of material, dental tray, sponge material or mixtures thereof. The delivery carrier may be attached to the teeth via the compositions herein or the adhesion function can be provided independent of the present compositions herein (e.g. can be provided via a separate adhesive composition used with the present compositions and delivery carrier).

The delivery carrier may be attached to the teeth via an attachment means that is part of the delivery carrier, for example the delivery carrier may optionally be of sufficient size that once applied the delivery carrier overlaps with the oral soft tissues rendering more of the teeth surface available for bleaching. The delivery carrier may also be attached to the oral cavity by physical interference or mechanical interlocking between the delivery carrier and the oral surfaces including the teeth.

DETAILED DESCRIPTION OF THE INVENTION

Figure 1:
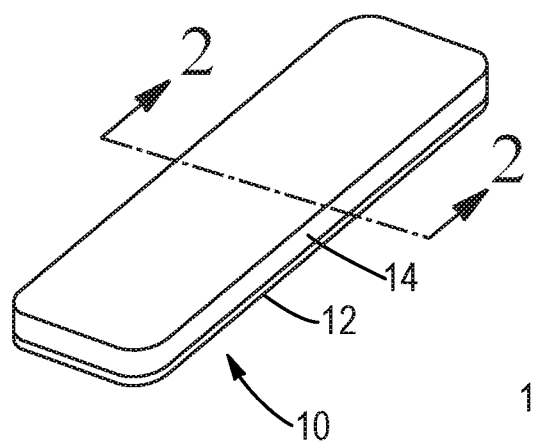
FIG. 1 is a perspective view of a delivery system 10 comprising a strip of material 12 having rounded corners upon which in a second layer 14 the present compositions are coated.

Without being bound to a theory it was surprisingly found that bleaching agents are effective in very low concentration, if presented in a multi-phase oral composition as disclosed herein. The present invention comprises in certain embodiments, from about 0.001% to about 80% of hydrophilic bleaching agent particles, and a hydrophobic phase; wherein the hydrophilic bleaching agent particles are soluble in water, swell upon contact with water, or release a bleaching agent upon contact with water.

The multi-phase composition can be a semisolid dispersion of hydrophilic bleaching agent particles in a liquid or semisolid hydrophobic phase. Without wishing to be bound by theory, it is believed that when a semisolid dispersion contacts the surface of a tooth, the hydrophilic particles stabilized within the dispersion may deliver bleaching agent to the hydrophilic biofilm on the surface of the tooth. This can lead to increased whitening efficacy with lower total levels of bleaching agent.

By "oral care composition", as used herein, is meant a product, which in the ordinary course of usage, is not intentionally swallowed for purposes of systemic administration of particular therapeutic agents, rather it is retained in the oral cavity for a time sufficient to contact dental surfaces or oral tissues. Examples of oral care compositions include dentifrice, tooth gel, subgingival gel, mouth rinse, mousse, foam, mouth spray, lozenge, chewable tablet, chewing gum, tooth whitening strips, floss and floss coatings, breath freshening dissolvable strips, denture care products, or denture adhesive products. The oral care composition may also be incorporated onto strips or films for direct application or attachment to oral surfaces.

The term "dentifrice", as used herein, includes tooth or subgingival—paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "immiscible" or "insoluble" as used herein means less than 1 part by weight of the substance dissolves in 100 parts by weight of a second substance.

The term "solubility" as used herein is the maximum number of parts by weight of the substance that can dissolve in 100 parts by weight of a second substance.

The term "phase" as used herein means a physically distinct region or regions, which may be continuous or discontinuous, having one or more properties that are different from another phase. Non-limiting examples of properties that may be different between phases include composition, viscosity, solubility, hydrophobicity, hydrophilicity, and miscibility. Examples of phases include solids, liquids, and gases.

The term "multi-phase oral composition" as used herein comprises a mixture of two or more phases that are immiscible with each other, for example a dispersion of hydrophilic bleaching agent particles in a hydrophobic phase. The phases may be continuous, discontinuous, or combinations thereof. Examples of multi-phase oral compositions include dispersions, such as suspensions and sols. The multi-phase oral composition or a phase of the multi-phase oral composition may be solid, liquid, semisolid, or combinations thereof. In certain embodiments the multi-phase oral composition as disclosed herein is semisolid. Examples of multi-phase oral compositions also include compositions where the phases are multi-continuous including bi-continuous, layered, striped, marbled, ribbons, swirled, and combinations thereof.

The term "dispersion" as used herein is an example of a multi-phase oral composition wherein: 1) at least one of the phases is discontinuous and 2) at least one of the phases is continuous. Examples of dispersions include hydrophilic bleaching agent particles dispersed in a hydrophobic phase. In this example the hydrophilic bleaching agent particles and hydrophobic phase would be immiscible with each other, the hydrophilic bleaching agent particles would be the discontinuous phase, and the hydrophobic phase would be the continuous phase.

The term "heterogenous mixture" as used herein is a heterogenous combination of two or more substances. Examples of heterogenous mixtures include hydrophilic bleaching agent particles dispersed in a hydrophobic phase. Heterogenous mixtures do not include homogenous mixtures (such as solutions where a solute is uniformly dissolved in a solvent).

The term "heterogenous dispersion" as used herein is a heterogenous combination of two or more substances. Examples of heterogenous dispersions include hydrophilic bleaching agent particles dispersed in a hydrophobic phase. Heterogenous dispersions do not include homogenous dispersions (such as solutions where a solute is uniformly dissolved in a solvent).

The term "particle" as used herein is a discrete, solid or semisolid material. Solid particles have dimensions larger than individual atoms or molecules and are typically submicron to about a millimeter in their largest dimension. In certain embodiments, particles may be agglomerated into an agglomerate of discrete particles. In certain embodiments particles may have dimensions or a number-average equivalent-diameter or volume-average equivalent-diameter from about 50 nm to about 1 mm.

The term "solid" as used herein is a material that, at room temperature, 1) has defined dimensions even when it is not constrained in a container, or 2) maintains its original shape when it is picked up off a surface and subsequently placed back on the surface. Examples of solids include urea peroxide, and complexes of hydrogen peroxide and polyvinylpyrrolidone polymers.

The term "preformed sheet" as used herein refers to a composition which has been formed into a sheet suitably shaped to fit into an oral cavity. Preformed sheets are solid once formed.

The term "stick type product" as used herein refers to a composition which is a bar of an apparently firm solid material held within a dispensing container which when applied to a surface to be treated, retains its structural integrity and shape. When a portion of the stick is drawn across a surface, a film of the stick composition is transferred to the surface. Examples include lip balm and lipstick.

The term "liquid" as used herein is a material that, at room temperature, 1) flows under gravity, or 2) takes the shape of the container it is placed in. Examples of liquids include mineral oil, water, and silicone oil.

The term "semisolid" as used herein is a material that, at room temperature, 1) has some solid-like properties and some liquid-like properties, or 2) whose ability to meet the above definition of a solid or liquid may depend on the amount of material being evaluated—for example, a small amount of petrolatum placed in a large container may not flow under gravity, and it may not take the shape of the container (thus not meeting the definition of a liquid); but a large amount of petrolatum placed in an large container may flow under gravity, or it may take the shape of the container (thus meeting the definition of a liquid). Examples of semisolids include petrolatum, toothpaste, silicone gels, mayonnaise, lotion, and butter. Examples of semisolids may also include materials that have a cone penetration consistency value from about 10 to about 500, from about 25 to about 300, from about 50 to about 250, or from about 100 to about 200 measured according to ASTM 937. Example of semisolids may also include materials that have a melting point or drop melting point as measured according to ASTM method D127 or a congealing point as measured according to ASTM method D938 from about from about 40° C. to about 120° C., from about 50° C. to about 100° C., from about 500 to about 90° C., or from about 60° C. to about 80° C. In certain embodiments, semisolids may not include stick type products or a bar of an apparently firm solid material held within a dispensing container which when applied to a surface to be treated, retains its structural integrity and shape.

The term "particles-in-semisolid dispersion" as used herein is an example of a dispersion wherein particles are dispersed in a semisolid phase. Examples of particles-in-semisolid dispersions include hydrophilic bleaching agent particles dispersed in petrolatum.

The term "hydrophilic bleaching agent particle" as used herein is a particle that a) comprises a bleaching agent, and b) is soluble in water, swells (increase in volume and/or weight) upon contact with water or releases a bleaching agent upon contact with water. If a bleaching agent is released, the bleaching agent may be a gas, liquid, or solid dissolved in a liquid. In certain embodiments the hydrophilic bleaching agent particle is insoluble in the hydrophobic phase. In certain embodiments the hydrophilic bleaching agent particles or multi-phase oral composition may further comprise ingredients that are water soluble, water miscible, or combinations thereof, such as for example water water-soluble solvents, alcohols, carbopol, polyalkylene glycols, humectants, glycerin, sorbitol, xylitol, butylene glycol, polyethylene glycol, and propylene glycol, and mixtures thereof. In certain embodiments, the hydrophilic bleaching agent particles may also include water of hydration or solvents of crystallization. If these ingredients are added to or present in the hydrophilic bleaching agent particles, the percentage of the hydrophilic bleaching agent particles in the composition is calculated by excluding these ingredients. If water-insoluble or water-immiscible fillers are added to the hydrophilic bleaching agent particles or multi-phase oral composition, the percentage of the hydrophilic bleaching agent particles in the composition is calculated by excluding these fillers.

The term "bleaching agent" as used herein is a component of the bleaching agent particle that bleaches. For example, if urea peroxide (also known as urea hydrogen peroxide adduct) is used as a bleaching agent particle, the hydrogen peroxide component of the urea peroxide particle is a bleaching agent. Similarly, if a complex of hydrogen peroxide and polyvinylpyrrolidone (PVP) polymer is used as a bleaching agent particle, the hydrogen peroxide component of the complex of hydrogen peroxide and polyvinylpyrrolidone (PVP) polymer is a bleaching agent.

The term "hydrophobic phase" as used herein means all components of the composition that are immiscible with water. In certain embodiments the hydrophobic phase is insoluble in water. In certain embodiments, the hydrophobic phase may further comprise ingredients that are soluble, miscible or combinations thereof in the hydrophobic phase, such as for example hydrocarbon solvents dissolved into the hydrophobic phase, polyethylene dissolved into the hydrophobic phase, microcrystalline wax dissolved into the hydrophobic phase, or mixtures thereof. In certain embodiments the hydrophobic phase is semisolid. If water-insoluble or water-immiscible fillers are added to the hydrophilic bleaching agent particles or multi-phase oral composition, the percentage of the hydrophobic phase in the composition is calculated by including these fillers as a part of the hydrophobic phase.

The term "petrolatum" as used herein means a semisolid mixture of hydrocarbons. Petrolatum may have a cone penetration consistency value as measured according ASTM method D937 from about 10 to about 500, from about 25 to about 300, from about 50 to about 250, or from about 100 to about 200. Petrolatum may have a melting point or drop melting point as measured according to ASTM method D127 or a congealing point as measured according to ASTM method D938 from about from about 40° C. to about 120° C., from about 50° C. to about 100° C., from about 50° to about 90° C., or from about 60° C. to about 80° C.

The term "cone penetration consistency value" as used herein means the depth, in tenths of a millimeter, that a standard cone will penetrate the sample under fixed conditions of mass, time, and temperature. The cone penetration consistency value is measured according to ASTM method D937.

The term "delivery carrier" as used herein comprises a material or an appliance that is used to hold the multi-phase oral composition against the tooth surface. Examples of delivery carriers include strips or dental trays.

The term "strip" as used herein comprises a material 1) whose longest dimension length is generally greater than its width, and 2) whose width is generally greater than its thickness. Strips may be rectangular, arched, curved, semicircular, have rounded corners, have slits cut into it, have notches cut into it, bent into three dimensional shapes, or combinations thereof. Strips may be solid, semi-solid, textured, moldable, flexible, deformable, permanently deformable, or combinations thereof. Strips may be made from plastic sheets including polyethylene, or wax sheets. Examples of strips include a piece of polyethylene about 66 mm long, 15 mm wide and 0.0178 mm thick. Examples of permanently deformable strips include a piece of casting wax sheet about 66 mm long, 15 mm wide, and 0.4 mm thick.

The multi-phase oral compositions herein, which may be particles-in-semisolid dispersions, are useful for topical application, in particular for topical application in the mouth. For example, the composition might be an oral care composition.

As used herein, the word "or" when used as a connector of two or more elements is meant to include the elements individually and in combination; for example X or Y, means X or Y or both.

As used herein, the articles "a" and "an" are understood to mean one or more of the material that is claimed or described, for example, "an oral care composition" or "a bleaching agent."

By "safe and effective amount" as used herein means an amount of a component, high enough to significantly (positively) modify the condition to be treated or to affect the desired whitening result, but low enough to avoid serious side effects (at a reasonable benefit/risk ratio), within the scope of sound medical/dental judgment. The safe and effective amount of a component, will vary with the particular condition being treated, the age and physical condition of the patient being treated, the severity of the condition, the duration of treatment, the nature of concurrent therapy, the specific form employed, and the particular vehicle from which the component is applied.

By "a sufficient period of time to achieve whitening" as used herein is meant that the composition is used or worn by the participant or the participant is instructed to use or wear the composition for greater than about 10 seconds; or greater than about 1 minute, such as from about 2.5 minutes to about 12 hours (for example overnight treatment), or from about 3 minutes to about 180 minutes; or greater than about 5 minutes, such as from about 5 minutes to about 60 minutes; or greater than about 10 minutes, such as from about 10 minutes to about 60 minutes; or from about 1, 5, 10, or 15 minutes to about 20, 30, 60, 120 minutes per application; or any other numerical range, which is narrower and which falls within such broader numerical range, as if such narrower numerical ranges were all expressly written herein. In addition, the treatments may be applied from about 1, 2, or 3 times a day to about 4, 5, 6 or 7 times a day. The treatments may be applied for from about 1, 2, 3, 4, 5, 6, or about 7 days to about 8, 9, 10, 11, 12, 13, 14, 21, or 28 days or any other numerical range, which is narrower and falls within such broader numerical range, as if such narrower numerical ranges were all expressly written herein. Further, the length of treatment to achieve the desired benefit, for example, tooth whitening, may last for a specified period of time, which may be repeated if necessary, for example from about one day to about six months, in particular from about one day to about 28 days, or from about 7 to about 28 days. The optimal duration and frequency of application will depend on the desired effect, the severity of any condition being treated, the health and age of the user and like considerations.

The term "dispenser", as used herein, means any pump, tube, or container suitable for dispensing oral care compositions.

By "μm" or "microns" as used herein is meant micrometer.

The term "equivalent diameter" of a particle as used herein means the diameter of a sphere having the same volume as the particle.

All percentages and ratios used herein after are by weight of total composition (wt %), unless otherwise indicated. All percentages, ratios, and levels of ingredients referred to herein are based on the actual amount of the ingredient, and do not comprise solvents, fillers, or other materials with which the ingredient may be combined as a commercially available product, unless otherwise indicated.

All measurements referred to herein are made at about 23° C. (i.e. room temperature) unless otherwise specified.

"Active and other ingredients" useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

The term "teeth", as used herein, refers to natural teeth as well as artificial teeth or dental prosthesis and is construed to comprise one tooth or multiple teeth. The term "tooth surface" as used herein, refers to natural tooth surface(s) as well as artificial tooth surface(s) or dental prosthesis surface(s) accordingly.

The term "orally acceptable carrier" comprises one or more compatible solid or liquid excipients or diluents which are suitable for use in the oral cavity. By "compatible," as used herein, is meant that the components of the composition are capable of being commingled without interaction in a manner which would substantially reduce the composition's stability and/or efficacy.

Multi-Phase Oral Compositions

The multi-phase oral compositions, as disclosed herein, comprise hydrophilic particles dispersed in a hydrophobic phase. The multi-phase oral composition, as disclosed herein, can be a semisolid dispersion comprising hydrophilic bleaching agent particles dispersed in a hydrophobic phase.

For dispersions comprising hydrophilic bleaching agent particles, the size of the particles of the hydrophilic bleaching agent particles may be a factor to decrease oral/topical irritation, decrease tooth-sensitivity, or increase bleaching efficacy. Without being bound by theory, if the size of the hydrophilic bleaching agent particles is too large it may lead to large spots on oral/topical/tooth surfaces that are exposed to a high concentration of the bleaching agent, which in turn may lead to oral/topical irritation and/or tooth-sensitivity. The number-average equivalent-diameter, surface-area-average equivalent-diameter, or volume-average equivalent-diameter of the hydrophilic bleaching agent particles may be no more than about 0.001 micron, 0.01 micron, 0.1 micron, 1 micron, 5 microns, 10 microns, 50 microns, 100 microns, 500 microns, or 1000 microns or any other numerical range, which is narrower and which falls within such broader numerical range, as if such narrower numerical ranges were all expressly written herein. The number-average equivalent-diameter, surface-area-average equivalent-diameter, or volume-average equivalent-diameter of the hydrophilic bleaching agent particles may be from about 0.001 micron to about 1000 microns, preferably from about 0.01 micron to about 1000 microns, more preferably from about 0.1 micron to about 100 microns, and most preferably from about 1 to about 100 microns or any other numerical range, which is narrower and which falls within such broader numerical range, as if such narrower numerical ranges were all expressly written herein.

Compositions that have a high density of large hydrophilic bleaching agent particles may lead to oral/topical irritation and/or tooth-sensitivity. Thus, the two-dimensional density of the hydrophilic bleaching agent particles with a cross-sectional area larger than about 1000, 3000, 10000, 20000, or 50000 square microns may be no more than about 0.5, 1, 2, 3, 4, 5, 6, 7, 8, 9, 10, 15, 20, 25, 50, or 100 per square centimeter of the two-dimensional plane, or any other numerical range, which is narrower and which falls within such broader numerical range as if such narrower numerical ranges were all expressly written herein. The two-dimensional density of hydrophilic bleaching agent particles with a cross-sectional area larger than about 10000 square microns may be no more than about 25, preferably no more than 10, more preferably no more than 5, and most preferably no more than 1 per square centimeter of the two-dimensional plane or any other numerical range, which is narrower and which falls within such broader numerical range as if such narrower numerical ranges were all expressly written herein.

The components and properties of the hydrophilic bleaching agent particles and the hydrophobic phase can be chosen to allow for the release of the bleaching agent readily from the composition.

Without wishing to being bound by theory, it is believed that when the present invention, such as hydrophilic particles-in-semisolid dispersion, is brought into contact with a tooth surface, the hydrophilic bleaching agent particles may deliver bleaching agent to the hydrophilic biofilm on the surface of the tooth. The possible net effect is that the teeth whitening effect is started only after contact with the tooth surface to be treated. That means, the bleaching agent may be protected against environmental influence and thereby stabilized by the hydrophobic phase of the multi-phase oral composition until use and potentially by the hydrophobic phase in the form of a film or layer during use. Thereby, the active effect may be applied to the tooth surface and the active agent, e.g. the bleaching agent may be potentially shielded against the oral environment during use. Thereby the efficacy of a whitening multi-phase oral composition may be enhanced and/or accelerated.

Without wishing to being bound by theory, the present invention may improve the delivery of the whitening agent to the tooth surface and thus the whitening performance due to the partial hydrophobic and partial hydrophilic nature of the composition. Upon contact between the multi-phase composition and a tooth surface, the hydrophilic bleaching agent particles within the multi-phase composition may be driven towards the tooth surface. Thus, the speed of whitening and the efficacy of the bleaching agent can be increased with surprisingly low concentrations of bleaching agents. The present invention, therefore, at a given total overall concentration, such as 0.1%, 1%, or 5%, by weight or below of a bleaching agent, may deliver a surprisingly high level of whitening efficacy, may require fewer applications to get the same degree of whitening, or may require a lower gel load (milligrams of gel per unit area) to get the same degree of whitening.

Without wishing to be bound by theory, it is believed that part of the reason for the high efficacy delivered by multi-phase oral compositions of the present invention may be because in certain embodiments they are self-adhesive or self-substantive to teeth, and resistant to being washed away in saliva or other liquids. This may keep the active agents or bleaching agents in contact with the oral surface such as the tooth surface or in the oral cavity for a long time, thus leading to high efficacy. It is worth noting that in general substances that are adhesive or substantive to the oral cavity are hydrophilic because surfaces in the oral cavity are wet. It is also worth noting that some product forms, especially stick type products, may need an added substantivity agent to adhere the composition to surfaces in the oral cavity. However, in certain embodiments, it has been surprisingly discovered that the multi-phase oral composition of the present invention and/or the hydrophobic phase of the present invention are self-adhesive or self-substantive to surfaces in the oral cavity such as tooth surfaces even without an added adhesive (for example hydrophilic particles that become sticky when activated by moisture, or hydrophilic liquids) or added substantivity agent. Achieving adhesiveness or substantivity without the use of an added hydrophilic adhesive or hydrophilic substantivity agent is particularly useful because it may help make the multi-phase oral composition resistant to being washed away in saliva or other liquids—thus leading to higher efficacy. This is because achieving adhesiveness or substantivity without the use of an added hydrophilic adhesive or added hydrophilic substantivity agent can allow us to increase the level of hydrophobic components (that resist being washed away) and/or decrease the level of hydrophilic components (that are susceptible to being washed away). Counterintuitively, this can help increase the substantivity of the multi-phase oral composition leading to a high concentration of the active agent or bleaching agent in contact with the oral surface such as the tooth surface or in the oral cavity for a long time, this in turn leading to high efficacy. Furthermore, without wishing to be bound by theory, it is believed that hydrophilic liquids may also leach out of the multi-phase oral composition and lead to macroscopic separation of one or more of the components at temperatures (for example −7 C, 4 C, 23 C, 25 C, 30 C, 40 C, 50 C, or 60 C) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer. This is because hydrophilic liquids may be repelled by the hydrophobic phase and forced out of the multi-phase oral composition. Thus, in certain embodiments, the multi-phase oral composition of the present invention and/or the hydrophobic phase of the present invention are substantially free of an added adhesive, preferably substantially free of an added hydrophilic adhesive (for example hydrophilic particles that become sticky when activated by moisture) or an added hydrophilic substantivity agent, and more preferably substantially free of an added hydrophilic liquid adhesive (for example glycerin). In certain embodiments, the multi-phase oral composition of the present invention and/or the hydrophobic phase of the present invention are self-adhesive or self-substantive to the oral cavity such as the tooth surface.

It is also worth noting that some product forms, especially stick type products, may need an added active releasing agent or added peroxide releasing agent to improve the release of the active or peroxide trapped in the stick type product. In general, active releasing agents or peroxide releasing agents are hydrophilic water-soluble or water-swellable polymers or hydrophilic liquids that may provide hydration channels in the composition allowing water to penetrate the composition and allowing the active or peroxide to leach out. In certain embodiments, an added peroxide releasing agent (such as sodium percarbonate) may help break the hydrophobic matrix as a result of micro bubbles that may be generated when the it comes in contact with water; and this disruption may enhance the release of the whitening agents, such as the hydrogen peroxide. However, in certain embodiments, it has been surprisingly discovered that the multi-phase oral compositions of the present invention are self-releasing (for example, they release active or peroxide even without an added active releasing agent or an added peroxide releasing agent). Achieving active or peroxide release without the use of an added hydrophilic active releasing agent or added hydrophilic peroxide releasing agent is particularly useful because it may help make the multi-phase oral composition resistant to being washed away in saliva or other liquids—thus leading to high efficacy. This is because achieving active or peroxide release without the use of an added hydrophilic active releasing agent or added hydrophilic peroxide releasing agent allows us to increase the level of hydrophobic components (that resist being washed away) and/or decrease the level of hydrophilic components (that are susceptible to being washed away). Thus, in certain embodiments, the multi-phase oral compositions of the present invention of the present invention are substantially free of an added active releasing agent or added peroxide releasing agent, preferably substantially free of an added hydrophilic active releasing agent or added hydrophilic peroxide releasing agent (for example water-soluble or water-swellable polymers, hydrophilic liquids, or sodium percarbonate). In certain embodiments, the multi-phase oral composition of the present invention and/or the hydrophobic phase of the present invention are self-releasing (i.e. they release active or peroxide even without an added active releasing agent or an added peroxide releasing agent).

In certain embodiments, if the multi-phase oral composition of the present invention comprises an added adhesive, added hydrophilic adhesive, added hydrophilic liquid adhesive, added hydrophilic substantivity agent, added hydrophilic active releasing agent, or added hydrophilic peroxide releasing agent, it may be present in a range from about 0, 0.1, 0.2, 0.4, 1, 2, 3, 4, 5, to about 0, 0.1, 0.2, 0.4, 1, 2, 3, 4, 5, 6, 7, 8, 9, 10, 20% or any other numerical range which is narrower and which falls within such broader numerical range, as if such narrower numerical ranges were all expressly written herein; preferably less than about 20%, more preferably less than about 10%, even more preferably less than about 5%, or most preferably less than about 0.5% by weight of the multi-phase oral composition.

In addition, retention of the multi-phase oral composition on the tooth surfaces may be improved as the hydrophobic phase resists salivary dilution and salivary enzymes which can decompose the peroxide. Even furthermore, the hydrophobic phase likely does not dehydrate the teeth creating an outward flux of water created by many hydrophilic compositions containing hydrophilic adhesives such as polycarboxylic acid. Since the hydrophobic phase likely does not dehydrate the teeth it may result in a surprisingly low level of tooth sensitivity even while delivering a surprisingly high level of whitening efficacy.

In addition, the hydrophobic phase may provide further advantages. For example, the hydrophobic phase represents a stable matrix for ingredients which are soluble in the hydrophobic phase. For example, many flavor ingredients usually used in oral compositions are soluble in the hydrophobic phase. That means the flavor ingredients may be protected from any influence of the active agent, for example the bleaching agent, in the oral composition. In addition, during use of the oral composition at the tooth surface at least part of the hydrophobic phase may be located—without being bound by theory—towards the soft oral tissues, such as the mucosa, thereby presenting the ingredients which are present in the hydrophobic phase, such as flavor compounds, to the oral cavity. In addition, the hydrophobic phase may shield the active agent, such as the bleaching agent against any influence from the oral cavity, such as dilution by saliva. The shielding effect may also apply to the tooth surface(s) themselves, wherein the hydrophobic phase may provide greater hydration of the teeth surfaces.

In certain embodiments, multi-phase oral compositions of the present invention may be paste, cream, gel, semisolid, viscoelastic gel, sol, or any combination thereof.

It is worth noting that stick type products may be unhygienic for repeated use inside the oral cavity due to potential contamination or bio-film build-up. Saliva or moisture may penetrate into the stick type composition when used inside the oral cavity and this may degrade the active agents especially bleaching agents such as peroxides during storage between uses; and this degradation may be further accelerated by enzymes present in saliva. Furthermore, this degradation could be most pronounced at the tip of the stick type product that comes in direct contact with the saliva or moisture inside the oral cavity, leading to diminished efficacy the next time the stick type product is used. This "contact-degrade-contact" cycle may be repeated every time the stick type product is used—leading to most if not all applications after the first application being less efficacious. It is also worth noting that stick type products may need an added active releasing agent or added peroxide releasing agent to improve the release of the active or peroxide trapped in the stick type product. In general, active releasing agents or peroxide releasing agents are hydrophilic water-soluble or water-swellable polymers or hydrophilic liquids that may provide hydration channels in the composition allowing water to penetrate the composition and allowing the active or peroxide component to leach out. However, these channels may also allow more saliva to penetrate into the composition which may accelerate the degradation of the active or peroxide.

It is worth noting that multi-phase oral compositions in liquid form may exhibit macroscopic separation of one or more components due to differences in the density of the phases. Specifically, compositions that are particles dispersed in one or more liquids may exhibit macroscopic separation of one or more components due to the difference in density of the particles compared to liquids. Furthermore, multi-phase oral compositions in liquid form may not be substantive and run down the teeth or run out of the delivery carrier during application or during use.

Thus, in certain embodiments of the multi-phase oral compositions of the present invention, the stick type product or liquid form is less or not preferred. In certain embodiments, multi-phase oral compositions of the present invention may preferably be a paste, cream, gel, semisolid, or any combination thereof; and most preferably a semisolid.

In certain embodiments, the multi-phase oral compositions of the present invention are substantially free of an added wax since it may promote the formation of stick type products that are less or not preferred.

In certain embodiments, multi-phase oral compositions of the present invention may be a heterogenous mixture and/or heterogenous dispersion.

Hydrophilic Bleaching Agent Particles

The present multi-phase oral compositions comprise a safe and effective amount of hydrophilic bleaching agent particles, wherein the level of hydrophilic bleaching agent particles is based on the available oxygen or chlorine respectively that the molecule provides to bleach the stain. In certain embodiments, the maximum amount of hydrophilic bleaching agent particles may be about 0.01%, 0.02%, 0.03%, 0.04%, 0.05%, 0.06%, 0.07%, 0.08%, 0.09%, 0.095%, 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 47.5%, 50%, 60%, 70%, or 80% by weight of the multi-phase oral composition or any other numerical range, which is narrower and which falls within such broader numerical range, as if such narrower numerical ranges were all expressly written herein.

It has been surprisingly found that the solubility of the hydrophilic bleaching agent particles in water, ability to swell upon contact with water, or ability to release a bleaching agent upon contact with water, impacts the bleaching efficacy of the composition. In certain embodiments, at least about 80, 70, 60, 50, 40, 30, 25, or 20 parts by weight of the hydrophilic bleaching agent particles dissolves in about 100 parts by weight of water, or the hydrophilic bleaching agent particles swells by at least about 80%, 70%, 60%, 50%, 40%, 30%, 25%, or 20% upon contact with water. Without being bound by theory, surprisingly the amount of water available on the facial surface of the maxillary anterior teeth to hydrate the hydrophilic bleaching agent particles and release the bleaching ingredients is low compared to the rest of the oral cavity. This is particularly important because the facial surfaces of the maxillary anterior teeth are the ones that are most visible when smiling. Thus, the solubility of the hydrophilic bleaching agent particles in water, its ability to swell upon contact with water, or its ability to release a bleaching agent upon contact with water can impact the bleaching efficacy of the composition disproportionately on the "smile teeth" (facial surface of the maxillary anterior teeth).

Examples of hydrophilic bleaching agent particles include urea peroxide (also known as carbamide peroxide, or urea hydrogen peroxide adduct), and complexes of hydrogen peroxide and polyvinylpyrrolidone (PVP) polymers (also known as Peroxydone), and mixtures thereof.

Examples of hydrophilic bleaching agent particles include agents that provide bleaching effects, stain bleaching effects, stain removal effects, stain color change effects or any other effect, which change, or brighten tooth color. For example, in certain embodiments hydrophilic bleaching agent particles include a source of peroxide radicals. In addition, hydrophilic bleaching agent particles may include peroxides, metal chlorites, perborates, percarbonates, peroxyacids, persulfates, compounds that form the preceding compounds in situ, and combinations thereof. Examples of peroxide compounds may include urea peroxide, calcium peroxide, carbamide peroxide, and mixtures thereof. Examples of metal chlorites may include calcium chlorite, barium chlorite, magnesium chlorite, lithium chlorite, sodium chlorite, potassium chlorite, and mixtures thereof. Examples of hydrophilic bleaching agent particles may include hypochlorites (such as metal hypochlorites). Examples of persulfates may include salts of peroxymonosulfate, peroxydisulfate and mixtures thereof. Examples of persulfates, perborates, percarbonates, and hypochlorites include corresponding salts of sodium, calcium, potassium, and other metals.

In certain embodiments, the hydrophilic bleaching agent particles may be from about 0.001%, 0.01%, 0.02%, 0.03%, 0.04%, 0.05%, 0.06%, 0.07%, 0.08%, 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 47.5%, 50%, 60%, 70%, or 80% to about 0.001%, 0.01%, 0.02%, 0.03%, 0.04%, 0.05%, 0.06%, 0.07%, 0.08%, 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 47.5%, 50%, 60%, 70%, or 80% by weight of the multi-phase oral composition or any other numerical range, which is narrower and which falls within such broader numerical range, as if such narrower numerical ranges were all expressly written herein.

In certain embodiments the hydrophilic bleaching agent particles level may be less than 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% by weight of the multi-phase oral composition, in some embodiments less than 0.9%, 0.8%, 0.7%, 0.6%, 0.5%, 0.4%, 0.3%, 0.2%, or 0.1%, by weight of the multi-phase oral composition, or from about 0.1% to about 0.9%, or from about 0.2% to about 0.8%, or from about 0.3% to about 0.7% by weight of the multi-phase oral composition or any other numerical range, which is narrower and which falls within such broader numerical range, as if such narrower numerical ranges were all expressly written herein In certain embodiments, the hydrophilic bleaching agent particles may be from about 0.6% to about 10%, or from about 0.6% to about 6%, or from about 1% to about 5%, or from about 1% to about 3% by weight of the multi-phase oral composition or any other numerical range, which is narrower and which falls within such broader numerical range, as if such narrower numerical ranges were all expressly written herein.

The level of hydrophilic bleaching agent particles may be based on the available oxygen or chlorine respectively that the molecule provides to bleach a stain. In certain embodiments the hydrophilic bleaching agent particles level is less than or up to about 0.1% by weight of the multi-phase oral composition, in certain embodiments less than about 0.09%, 0.08%, 0.07%, 0.06%, 0.05%, 0.04%, 0.03%, 0.02%, 0.01%, or 0.001% by weight of the multi-phase oral composition, or from about 0.01% to about 0.099995%, from about 0.01% to about 0.095%, or from about 0.05% to about 0.09% by weight of the multi-phase oral composition, or any other numerical range, which is narrower and which falls within such broader numerical range, as if such narrower numerical ranges were all expressly written herein. Surprisingly, the hydrophilic bleaching agent particles are significantly effective when used even at the low levels in the multi-phase oral compositions as disclosed herein, which may be in the form of particles-in-semisolid dispersions.

In certain embodiments, the maximum amount of bleaching agent may be about 0.01%, 0.02%, 0.03%, 0.04%, 0.05%, 0.06%, 0.07%, 0.08%, 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 47.5%, 50%, 60%, 70%, or 80% by weight of the multi-phase oral composition or any other numerical range, which is narrower and which falls within such broader numerical range, as if such narrower numerical ranges were all expressly written herein.

In certain embodiments, the bleaching agent may be from about 0.001%, 0.01%, 0.02%, 0.03%, 0.04%, 0.05%, 0.06%, 0.07%, 0.08%, 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 47.5%, 50%, 60%, 70%, or 80% to about 0.001%, 0.01%, 0.02%, 0.03%, 0.04%, 0.05%, 0.06%, 0.07%, 0.08%, 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 47.5%, 50%, 60%, 70%, or 80% by weight of the multi-phase oral composition or any other numerical range, which is narrower and which falls within such broader numerical range, as if such narrower numerical ranges were all expressly written herein.

In certain embodiments the bleaching agent level may be less than 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% by weight of the multi-phase oral composition, in some embodiments less than 0.9%, 0.8%, 0.7%, 0.6%, 0.5%, 0.4%, 0.3%, 0.2%, or 0.1%, by weight of the multi-phase oral composition, preferably from about 0.1% to about 0.9%, more preferred from about 0.2% to about 0.8%, more preferred from about 0.3% to about 0.7% by weight of the multi-phase oral composition or any other numerical range, which is narrower and which falls within such broader numerical range, as if such narrower numerical ranges were all expressly written herein.

Ratio of Concentrations of Hydrogen Peroxide

In certain embodiments, the hydrophilic bleaching agent particles deliver hydrogen peroxide, by being an adduct or complex of hydrogen peroxide, or precursor to hydrogen peroxide. As such, they deliver a high ratio of the concentration in weight percent of hydrogen peroxide present in the hydrophilic bleaching agent particles to the concentration in weight percent of hydrogen peroxide present in the overall multi-phase oral composition. This results from the high concentration in weight percent of hydrogen peroxide present in the hydrophilic bleaching agent particles combined with a relatively low concentration in weight percent of hydrogen peroxide present in the overall multi-phase oral composition.

Without being bound by theory, in certain embodiments of the present invention comprising hydrogen peroxide, this surprising combination of seemingly contradictory parameters delivers the hydrogen peroxide to the tooth surface with a high driving force even when the overall concentration or amount of hydrogen peroxide delivered to the tooth surface is low. As a result, the high driving force delivers a surprisingly high level of bleaching efficacy and/or bleaching speed; while the low overall concentration or low amount of bleaching agent delivered to the tooth surface may help reduce tooth sensitivity.

In certain embodiments, the ratio of the concentration in weight percent of hydrogen peroxide present in the hydrophilic bleaching agent particles to the concentration in weight percent of hydrogen peroxide present in the overall multi-phase oral composition may be from about 50000, 35000, 20000, 17500, 10000, 5000, 3500, 2000, 1750, 1160, 1000, 875, 700, 580, 500, 430, 400, 380, 350, 200, 175, 111, 110, 105, 100, 90, 80, 70, 60, 50, 40, 30, 20, 15, 10, or 5 to about 50000, 35000, 20000, 17500, 10000, 5000, 3500, 2000, 1750, 1160, 1000, 875, 700, 580, 500, 430, 400, 380, 350, 200, 175, 111, 110, 105, 100, 90, 80, 70, 60, 50, 40, 30, 20, 15, 10, or 5 or any other numerical range, which is narrower and which falls within such broader numerical range, as if such narrower numerical ranges were all expressly written herein.

In certain embodiments, the ratio of the concentration in weight percent of hydrogen peroxide present in the hydrophilic bleaching agent particles to the concentration in weight percent of hydrogen peroxide present in the overall multi-phase oral composition may be at least or more than about 50000, 35000, 20000, 17500, 10000, 5000, 3500, 2000, 1750, 1160, 1000, 875, 700, 580, 500, 430, 400, 380, 350, 200, 175, 110, 105, 100, 90, 80, 70, 60, 50, 40, 30, 20, 15, 10, or 5 or any other numerical range, which is narrower and which falls within such broader numerical range, as if such narrower numerical ranges were all expressly written herein.

The bleaching agents of the present invention may be stabilized against degradation by the shielding effect of the hydrophobic phase.

Optional Stabilizing Agent for the Bleaching Agent

The multi-phase oral compositions of the present invention may comprise a stabilizing agent for the bleaching agent. The bleaching agent may be further stabilized against degradation by the multi-phase oral composition. Therefore, stabilizing agents may be added to the present composition. Suitable stabilizing agents are for example ortho-phosphoric acid, phosphate(s), such as sodium hydrogen phosphate, pyrophosphate(s), organophosphonate(s), Ethylenediaminetetraacetic acid, Ethylenediamine-N,N'-diacetic acid, Ethylenediamine-N,N'-disuccinic acid, potassium stannate, sodium stannate, tin salts, zinc salts, salicylic acid, 1-Hydroxyethylidene-1,1-diphosphonic acid, and combinations thereof. In certain embodiments, stabilizers may be used which show additional oral care effects, such as anti-tartar effect, produced by phosphates such as pyrophosphate, tripolyphosphate, hexametaphosphate, phytic acid, salts of $PO_3(PO_2)_nPO_3$ where n=2-30, phosphoric acid, gantrez, zinc salts including zinc citrate, zinc lactate, zinc chloride, zinc phosphate, zinc oxide, enzymes such as dextransses, xylanases, proteases, peroxides including hydrogen peroxide, urea peroxide and sodium percarbonate, phosphonates such as bis-phosphonate, chelants such as EDTA, Calcium Sodium EDTA, Citrate, citric acid, oxalic acid, oxalate salts, polymers (such as those disclosed in U.S. application Ser. No. 16/216,329), PVP, polyacrylic acid (carbopol), polyacrylates, stannous salts, stannic salts. In certain embodiments, a stabilizing agent may be present in a multi-phase oral composition of the present invention in an amount from about 0.0000001%, 0.000001%, or 0.00001%, to about 0.00001%, 0.0001%, or 0.01% by weight of the multi-phase oral composition or any other numerical range, which is narrower and which falls within such broader numerical range, as if such narrower numerical ranges were all expressly written herein. In certain embodiments, a stabilizing agent may be present in a multi-phase oral composition of the present invention in an amount from about 0.0001%, or 0.01% to about 0.01%, 0.1% or about 1% by weight of the hydrophilic bleaching agent particles or any other numerical range, which is narrower and which falls within such broader numerical range, as if such narrower numerical ranges were all expressly written herein.

A stabilizing agent may also include chelants. The chelant may be a copper, iron and/or manganese chelants, or a mixture thereof. Suitable chelants may be selected from: diethylene triamine pentaacetate, diethylene triamine penta (methyl phosphonic acid), ethylene diamine-N'N'-disuccinic acid, ethylene diamine tetraacetate, ethylene diamine tetra (methylene phosphonic acid), hydroxyethane di(methylene phosphonic acid), and any combination thereof. A suitable chelant may be selected from ethylene diamine-N'N'-disuccinic acid (EDDS), hydroxyethane diphosphonic acid (HEDP) or mixtures thereof. The stabilizer may comprise ethylene diamine-N'N'-disuccinic acid or salt thereof. The ethylene diamine-N'N'-disuccinic acid may be in S,S enantiomeric form. The stabilizer may comprise 4,5-dihydroxy-m-benzenedisulfonic acid disodium salt, glutamic acid-N,N-diacetic acid (GLDA) and/or salts thereof, 2-hydroxypyridine-1-oxide, Trilon P™ available from BASF, Ludwigshafen, Germany. Suitable chelants may also be calcium carbonate crystal growth inhibitors. Suitable calcium carbonate crystal growth inhibitors may be selected from the group consisting of: 1-hydroxyethanediphosphonic acid (HEDP) and salts thereof; N,N-dicarboxymethyl-2-aminopentane-1,5-dioic acid and salts thereof; 2-phosphonobutane-1,2,4-tricarboxylic acid and salts thereof; and any combination thereof.

A stabilizer may comprise a calcium carbonate crystal growth inhibitor, such as 1-hydroxyethanediphosphonic acid (HEDP); N,N-dicarboxymethyl-2-aminopentane-1,5-dioic acid; 2-phosphonobutane-1,2,4-tricarboxylic acid; and salts thereof; and any combination thereof.

A stabilizer may comprise a hydroxamate chelant. By 'hydroxamate' we herein mean hydroxamic acid or a corresponding salt, for example coco hydroxamic acid (Axis House RK 853).

Hydrophobic Phase

The present invention comprises a safe and effective amount of a hydrophobic phase. In certain embodiments, the present multi-phase oral compositions comprise a hydrophobic phase, wherein the hydrophobic phase may be at least or more than about 50%, 55%, 60%, 65%, 70%, 75%, 80%, 85%, 90%, 95%, 96%, 97%, 98%, 99%, 99.1%, or 99.5% by weight of the multi-phase oral composition or any other numerical range, which is narrower and which falls within such broader numerical range, as if such narrower numerical ranges were all expressly written herein.

In certain embodiments, the hydrophobic phase may be at least about 95%, 96%, 97%, 98%, 99%, 99.1%, or 99.5% by weight of the multi-phase oral composition or any other numerical range, which is narrower and falls within such broader numerical range, as if such narrower numerical ranges were all expressly written herein.

In certain embodiments, the present multi-phase oral compositions comprise a hydrophobic phase, wherein the hydrophobic phase may be more than about 50% by weight of the multi-phase oral composition.

In certain embodiments, the hydrophobic phase may be in predominant proportion relative to the hydrophilic bleaching agent particles present in the multi-phase oral composition. As used herein "predominant proportion" means that the percent by weight of the hydrophobic phase of the multi-phase oral composition is in excess relative to the percent by weight of the hydrophilic bleaching agent particles of the multi-phase oral composition.

The hydrophobic phase may be inert or at least partially inert. The hydrophobic phase may interact, but in certain embodiments does not interact or only minimally interacts with the other ingredients, such as for example, flavors or thickeners, in the multi-phase oral composition, including the bleaching agent.

A suitable hydrophobic phase for the compositions as disclosed herein may have an octanol/water partition coefficient (log $P_{ow}$) of greater than about 2, 3, 4, 5, or greater than about 5.5. In certain embodiments, the hydrophobic phase shows a log $P_{ow}$ greater than about 6 or any other numerical range, which is narrower and which falls within such broader numerical range, as if such narrower numerical ranges were all expressly written herein.

Without being bound by theory, the melting point, drop melting point, or congealing point of the hydrophobic phase may be a factor to ensure that the composition: 1) is substantive and does not run down the teeth or run out of the delivery carrier during application or during use, 2) inhibits macroscopic separation of one or more of the components at temperatures (for example −7 C, 4 C, 23 C, 25 C, 30 C, 40 C, 50 C, or 60 C) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer, or 3) releases an effective amount of the bleaching agent or active agent during use. Specifically, if the melting point, drop melting point, or congealing point of the hydrophobic phase is too low, the multi-phase oral composition may not be substantive and run down the teeth or run out of the delivery carrier during application or during use; or the multi-phase oral composition may exhibit macroscopic separation of one or more of the components at temperatures (for example −7 C, 4 C, 23 C, 25 C, 30 C, 40 C, 50 C, or 60 C) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer. In contrast, if the melting point, drop melting point, or congealing point of the hydrophobic phase is too high, the multi-phase oral composition may not release an effective amount of the bleaching agent or active agent during use. In certain embodiments, the melting point or drop melting point as measured according to ASTM method D127 or the congealing point as measured according to ASTM method D938 of a suitable hydrophobic phase may be in the range of from about 40° C. to about 120° C., from about 50° C. to about 100° C., from about 50 to about 90° C., or from about 60° C. to about 80° C., or any other numerical range, which is narrower, and which falls within such broader numerical range, as if such narrower numerical ranges were all expressly written herein. In certain embodiments, the melting point or drop melting point as measured according to ASTM method D127 or the congealing point as measured according to ASTM method D938 of the hydrophobic phase may be from about 120 C, 100 C, 90 C, 85 C, 80 C, 75 C, 70 C, 60 C, 50 C, 40 C, or 30 C, to about 100 C, 90 C, 85 C, 80 C, 75 C, 70 C, 60 C, 50 C, 40 C, 30 C, or 25 C, or any other numerical range, which is narrower, and which falls within such broader numerical range, as if such narrower numerical ranges were all expressly written herein.

Without being bound by theory, the cone penetration consistency value of the hydrophobic phase or the multi-phase oral composition may be a factor to ensure that the multi-phase oral composition: 1) is substantive and does not run down the teeth or run out of the delivery carrier during application or during use, 2) inhibits macroscopic separation of one or more of the components at temperatures (for example −7 C, 4 C, 23 C, 25 C, 30 C, 40 C, 50 C, or 60 C) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer, or 3) releases an effective amount of the bleaching agent or active agent during use. Specifically, if the cone penetration consistency value of the hydrophobic phase or the multi-phase oral composition is too high, the multi-phase oral composition may not be substantive and run down the teeth or run out of the delivery carrier during application or during use; or the multi-phase oral composition may exhibit macroscopic separation of one or more of the components at temperatures (for example −7 C, 4 C, 23 C, 25 C, 30 C, 40 C, 50 C, or 60 C) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer. In contrast, if the cone penetration consistency value of the hydrophobic phase or the multi-phase oral composition is too low, the multi-phase oral composition may not release an effective amount of the bleaching agent or active agent during use. It is worth noting that, in general: 1) hydrophobic phases that have a low cone penetration consistency value tend to form stick type products, especially when combined with powder ingredients including active agents or bleaching agents that are ground or manufactured to minimize particle size e.g. by micronization, 2) hydrophobic phases that are rich in waxes tend to have a low cone penetration consistency value, 3) stick type products tend to have a low cone penetration consistency value, 4) hydrophobic phases that have a low cone penetration consistency value (that tend to form stick type products) may also inhibit the release of the bleaching agent or active agent, and 5) stick type products (that tend to have a low cone penetration consistency value) may also inhibit the release of the bleaching agent or active agent. It is also worth noting that multi-phase oral compositions that have a low cone penetration consistency value or multi-phase oral compositions whose hydrophobic phase has a low cone penetration consistency value may be difficult or impractical to manually dispense a suitable dose of the multi-phase oral composition from a tube. Thus, in certain embodiments, the cone penetration consistency value of the hydrophobic phase or multi-phase oral compositions may optimally be in the range of from about 10 to about 500, from about 25 to about 300, from about 50 to about 250, or from about 100 to about 200, or any other numerical range, which is narrower and which falls within such broader numerical range, as if such narrower numerical ranges were all expressly written herein, and measured according to the methods specified herein.

In certain embodiments, the cone penetration consistency value of the hydrophobic phase or multi-phase oral composition may be from about 10, 25, 50, 100, 110, 120, 130, 140, 150, 160, 170, 180, 190, 200, 210, 220, 230, 240, 250, 300, 400, 500, 600, or 620 to about 25, 50, 100, 110, 120, 130, 140, 150, 160, 170, 180, 190, 200, 210, 220, 230, 240, 250, 300, 400, 500, 600, or 620, or any other numerical range, which is narrower, and which falls within such broader numerical range, as if such narrower numerical ranges were all expressly written herein, and as measured according to the methods specified herein.

Without being bound by theory, macroscopic separation of one or more of the components at temperatures (for example −7 C, 4 C, 23 C, 25 C, 30 C, 40 C, 50 C, or 60 C) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer may compromise the efficacy, safety, comfort, usage experience, concentration of actives or bleaching agents at the tooth surface over time, active or bleaching efficiency, or compatibility between ingredients. For example compositions that exhibit macroscopic separation of the hydrophilic bleaching agent particles or phases that contain a bleaching agent at temperatures (for example −7 C, 4 C, 23 C, 25 C, 30 C, 40 C, 50 C, or 60 C) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer may cause the concentration of bleaching agent to change from one dose to the other, and/or over time. This can compromise the efficacy, comfort, or usage experience (via oral irritation or tooth sensitivity for example) in certain doses; and this may vary from dose to dose, and/or over time. Specifically, if for example, a substantial portion of the bleaching agent particles have macroscopically separated into one phase, a dose that is disproportionately rich in this phase may cause oral irritation or tooth sensitivity when it comes in contact with the oral soft tissue or teeth. In contrast, if for example, a substantial portion of the hydrophobic phase has macroscopically separated into one phase, a dose that is disproportionately rich in this phase may have decreased bleaching efficacy. Both these conditions are undesirable because one leads to higher discomfort and the other leads to lower efficacy.

In certain embodiments the macroscopic separation of one or more of the components measured according to the method specified herein at temperatures (for example −7 C, 4 C, 23 C, 25 C, 30 C, 40 C, 50 C, or 60 C) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer may be from about 1%, 2%, 3%, 4%, 5%, 6%, 7%, 8%, 9%, 10%, 15%, 20%, 25%, or 50% to about 1%, 2%, 3%, 4%, 5%, 6%, 7%, 8%, 9%, 10%, 15%, 20%, 25%, or 50% or any other numerical range, which is narrower and which falls within such broader numerical range, as if such narrower numerical ranges were all expressly written herein.

In certain embodiments the macroscopic separation of one or more of the components measured according to the method specified herein after storage for 1 day, 2 days, 1 week, 2 weeks, 1 month, 2 months, 3 months, 6 months, 12 months, 18 months, or 24 months at 23 C+/−2 C may be from about 1%, 2%, 3%, 4%, 5%, 6%, 7%, 8%, 9%, 10%, 15%, 20%, 25%, or 50% to about 1%, 2%, 3%, 4%, 5%, 6%, 7%, 8%, 9%, 10%, 15%, 20%, 25%, or 50% or any other numerical range, which is narrower and which falls within such broader numerical ranges were all expressly written herein. In certain embodiments the macroscopic separation of one or more of the components measured according to the method specified herein after storage for 1 day, 2 days, 1 week, 2 weeks, 1 month, 2 months, 3 months, 6 months, 12 months, 18 months, or 24 months at 23 C+/−2 C may be no more than or less than about 1%, 2%, 3%, 4%, 5%, 6%, 7%, 8%, 9%, 10%, 15%, 20%, 25%, or 50%.

In certain embodiments the macroscopic separation of one or more of the components measured according to the method specified herein after storage for 2 days at 23 C+/−2 C may be from about 1%, 2%, 3%, 4%, 5%, 6%, 7%, 8%, 9%, 10%, 15%, 20%, 25%, or 50% to about 1%, 2%, 3%, 4%, 5%, 6%, 7%, 8%, 9%, 10%, 15%, 20%, 25%, or 50% or any other numerical range, which is narrower and which falls within such broader numerical range, as if such narrower numerical ranges were all expressly written herein. In certain embodiments the macroscopic separation of one or more of the components measured according to the method specified herein after storage for 2 days at 23 C+/−2 C may be no more than or less than about 1%, 2%, 3%, 4%, 5%, 6%, 7%, 8%, 9%, 10%, 15%, 20%, 25%, or 50%.

Method to Measure the Percent Macroscopic Separation of One or More Components of a Multi-Phase Oral Composition 1. Transfer 50 ml of the multi-phase oral composition into a 50 ml polypropylene conical tube (Falcon brand catalog number REF 352098, Corning Science, Tamaulipas, Mexico). If the multi-phase oral composition exhibits macroscopic separation of one or more components prior to transferring into the conical tube, mix the multi-phase oral composition in a Speedmixer (in a "Max 300 Long Cup Translucent", item number 501 218t from Flacktek Inc., Landrum, S.C.) (for example at 800 RPM for 2 minutes) and transfer into the conical tube before it exhibits macroscopic separation of one or more components. If the multi-phase oral composition has macroscopic air-bubbles or voids: 1) Tap the conical tube on a hard surface until it is free of macroscopic air-bubbles or voids, or 2) Use a different method to transfer the multi-phase oral composition into the conical tube such that it is substantially free of macroscopic air-bubbles or voids. Screw the cap onto the conical tube. Repeat for a total of three conical tubes.
2. Position all three conical tubes in a vertical orientation (for example in a test tube rack) with the conical end on the bottom and the cap on top.
3. Allow all three conical tubes to stay undisturbed in the vertical position in a room or chamber in which the air is maintained at the temperature (for example −7 C, 4 C, 23 C, 25 C, 30 C, 40 C, 50 C, or 60 C) for the period of time after which the macroscopic separation is to be measured.
4. At the end of period of time after which the macroscopic separation is to be measured (for example 1 day, 2 days, 1 week, 2 weeks, 1 month, 2 months, 3 months, 6 months, 12 months, 18 months, or 24 months) in the vertical position, measure the volume of material that has macroscopically separated on the bottom of the conical tube (aided by the graduations on the conical tube). If the volume of material that has macroscopically separated on the bottom of the conical tube is greater than 25 ml, measure the volume of material that has macroscopically separated to the top of the conical tube.
   Calculate the average volume of material that has macroscopically separated in all three tubes.

Assess the tube to tube variability of the volume of material that has macroscopically separated as follows: The volume of material that has separated in each and every tube must be within the range of +/−2.5 ml of the average. If the volume of material that has separated in any one or more of the tubes is outside the range of +/−2.5 ml of the average: This is an indication of sample to sample variability potentially due to macroscopic separation of one or more components prior to transferring into the conical tubes, and the method needs to be repeated starting at step-1 to minimize sample to sample variability.

5. Calculate the percent macroscopic separation as: 100× (average volume of material that has macroscopically separated measured and calculated in step-4 DIVIDED by 50 ml).

To validate the above method, the percent macroscopic separation of one or more components of the validation composition specified below must be measured and demonstrated to be from 6% to 10%.

| VALIDATION COMPOSITION FOR METHOD TO MEASURE PERCENT MACROSCOPIC SEPARATION | (Wt %) |
|---|---|
| 35% aqueous solution $H_2O_2$[1] | 1.43 |
| Sterile Filtered Water[2] | 4.24 |
| Aerosol OT[3] | 1.00 |
| Mineral Oil[4] | 93.33 |

[1] ultra Cosmetic Grade from Solvay, Houston, Texas
[2] Calbiochem catalog number 4.86505.1000 from EMD Millipore Corporation, Billerica, Massachusetts
[3] Aerosol OT-100 from Cytec Industries, Princeton, NJ
[4] White mineral oil Kaydol grade from Sonneborn LLC, Petrolia, Pennsylvania Procedure to Make the Validation Composition for Method to Measure Percent Macroscopic Separation A 175 gram batch of the validation composition is made by the following procedure:

a) 1.75 grams of the Aerosol OT and 163.33 grams of mineral oil are weighed into a Speedmixer container ("Max 300 Long Cup Translucent", item number 501 218t from Flacktek Inc., Landrum, S.C.).

b) The mixture is heated in an oven and mixed to dissolve the Aerosol OT in the mineral oil. This may be done by heating in an oven at 60° C. to 70° C. and mixing by hand-swirling or in a Speedmixer at 800 RPM for 2 minutes and repeating until the Aerosol OT is dissolved in the mineral oil.

c) In a separate plastic container, 42.4 grams of sterile filtered water and 14.3 grams of 35% aqueous solution of $H_2O_2$ are weighed, and swirled together. 9.92 grams of this diluted solution of $H_2O_2$ in water is weighed into the Speedmixer container.

d) The contents of the Speedmixer container are mixed in a Speedmixer at 800 RPM for 2 minutes. The walls of the container are then scraped down with a plastic spatula, and the contents are mixed a second time at 800 RPM for 2 minutes. The walls of the container are then scraped down with a plastic spatula, and the contents are mixed a third time at 800 RPM for 2 minutes.

Without being bound by theory, for multi-phase oral compositions that comprise peroxide, the mean residual peroxide concentration of the multi-phase oral composition smeared on teeth may be a factor to ensure that the multi-phase oral composition: 1) is substantive and does not wash away during use; and 2) still releases an effective amount of the bleaching agent during use. Specifically, if the mean residual peroxide concentration of the multi-phase oral composition on a tooth surface is too low, the multi-phase oral composition may not be substantive and wash away during use, or not release an effective amount of the bleaching agent during use. In certain embodiments, the mean residual peroxide concentration of a multi-phase oral composition smeared on teeth measured using the procedure specified herein may be from about 1, 2, 5, 10, 15, 20, 25, 30, 35, 40, 45, 50, 55, 60, 65, 70, 75, 80, 85, 90, 95, 100, 125, 150, 175, 200, or 225 to about 2, 5, 10, 15, 20, 25, 30, 35, 40, 45, 50, 55, 60, 65, 70, 75, 80, 85, 90, 95, 100, 125, 150, 175, 200, or 225 or any other numerical range, which is narrower and which falls within such broader numerical range, as if such narrower numerical ranges were all expressly written herein. In certain embodiments, the mean residual peroxide concentration of a multi-phase oral composition smeared on teeth measured using the procedure specified herein may be from about 1 to about 200, preferably from about 10 to about 200, more preferably from about 50 to about 200, and most preferably from about 100 to about 200, or any other numerical range, which is narrower and which falls within such broader numerical range, as if such narrower numerical ranges were all expressly written herein.

Method to Measure the Mean Residual Peroxide Concentration of a Composition Smeared on Teeth 1. Cut a circular disc (7.5 to 7.8 mm diameter×1.2 to 1.3 mm thickness) out of the front surface of a human incisor tooth. Leave the front surface intact but flatten the back surface that has been cut out of tooth using sand paper. Soak the tooth-disc in 15 to 20 ml of water that meets USP specification in a glass vial for at least 24 hours. Take the tooth-disc out of the water and place it on a fresh paper towel with the front surface facing upward.

2. Weigh 290 to 310 grams of water that meets USP specifications into a cylindrical plastic container with a screw-top lid 82 to 107 mm in diameter×106 to 108 mm height ("Max 200 Long Cup Translucent", item number 501 220t from Flacktek, Landrum, S.C.). Pre-heat the water in the container with the lid screwed on tight in a convection oven with air temperature at 33 C to 35 C for at least 12 hours.

3. Weigh 0.04 to 0.06 gram of the composition onto the tip of a disposable lip gloss applicator ("Flocked Doe Foot Lip Gloss Applicator" made of Nylon and Polystyrene, purchased from Qosmedix Inc., Ronkonkoma, N.Y., catalog number 74111).

4. Smear the composition onto the front surface of the wet tooth-disc by first rolling the tip of the lip gloss applicator loaded with the composition on the front surface of the tooth-disc to transfer the composition onto the tooth-disc and then fanning out toward the circular edge.

5. Pick up the tooth-disc with a tweezer. Make sure the tweezer touches only the circular edge of the tooth-disc and not the surface of the tooth-disc smeared with the composition. Tilt the plastic container and gently place the tooth-disc in the water on the cylindrical wall of the container where the cylindrical wall and flat bottom meet. Make sure the treated surface of the tooth-disc is facing upward away from the cylindrical wall of the container.

6. Place the cylindrical container on a roller mixer (model number TSRT9 by Techne purchased from VWR, Batavia, Ill., catalog number 89132-186; or item number 04750-30 from Cole-Parmer Inc., Vernon Hills, Ill.). Turn on the roller mixer—this gently rotates the container at 12 to 14 RPM. The tooth-disc should continue to remain immersed in the water and the treated surface should continue to face away from the rotating cylindrical wall. This rotating motion causes the water to flow gently over the tooth-disc similar to the gentle movement of saliva and other liquids over teeth in the mouth.

7. After 58 to 62 minutes shut off the roller mixer, take a fresh peroxide test strip (supplied by EMD Millipore Corporation, Billerica, Mass., supplier number 1.16974.0001; purchased from VWR, Batavia, Ill., catalog number EM1.16974.0001) out of the container, and start a timer.

8. Take a digital image of the peroxide test strip. The equipment and system configuration used to take the digital image of the test strip are specified herein.

9. Remove the tooth-disc from the water using a tweezer. As before, make sure the tweezer touches only the circular edge of the tooth-disc and not the surface of the tooth-disc smeared with the composition. Place the tooth-disc on a gloved finger-tip. Make sure the surface of the tooth-disc smeared with the composition is facing upward away from the gloved finger-tip.

10. Place the peroxide test strip against the tooth-disc such that one of the reaction-zones contacts the surface of the tooth-disc with the residual composition. Pinch the peroxide test strip against the tooth-disc between thumb and forefinger and apply firm finger pressure between thumb and forefinger for 2 to 3 seconds.

11. Move the peroxide test strip to a clean area of a paper towel. Place a filter paper (Whatman Grade 1 Qualitative Filter Paper Standard Grade, circle, 90 mm, supplier number 1001-090; purchased from VWR, Batavia, Ill., catalog number 28450-081) on top of the test strip. Apply finger pressure on top of the filter paper. Pull the peroxide test strip out from under the filter paper (while maintaining finger pressure on the filter paper) in a single stroke such that excess gel is wiped off onto the filter paper and paper towel. Make sure the reaction-zones do not get dislodged from the peroxide test strip.

12. Take a digital image of the peroxide test strip. The equipment and system configuration used to take the digital image of the test strip are specified herein.

13. Steps 7 to 12 must be completed within 3 minutes on the timer.

14. Repeat steps 1 to 13 for a minimum of twelve teeth.

15. Use Adobe Photoshop CS4 with the procedure specified herein to measure the mean and standard deviation of the RED intensities of the strip of Munsell N8 Matte Color sheet attached to the holder that serves as a built-in Munsell N8 reference within each image. The mean RED intensity of the built-in Munsell N8 reference within each image should be from 204 to 212 and the standard deviation should be no more than 3.

16. Use Adobe Photoshop CS4 with the procedure specified herein to measure the mean of the RED intensities of the reaction-zone on all peroxide test strips at BASELINE (before pressing against the tooth-disc).

17. Use Adobe Photoshop CS4 with the procedure specified herein to measure the mean of the RED intensities of same the reaction-zone on all peroxide test strips AFTER pressing against the tooth-disc.

18. The mean residual peroxide concentration of a composition smeared on teeth is calculated as follows: First, calculate the mean baseline RED intensity of each reaction-zone from step-16 MINUS the mean RED intensity of the same reaction-zone after pressing with the residual composition on the tooth-disc from step-17. Repeat this calculation for all reaction-zones pressed against the tooth-disc, and average the results. This is the mean residual peroxide concentration of a composition smeared on teeth.

In certain embodiments, the density of the hydrophobic phase used in the multi-phase oral compositions of the present invention is in the range of from about 0.8 g/cm to about 1.0 g/cm$^3$, from about 0.85 g/cm$^3$ to about 0.95 g/cm$^3$, or about 0.9 g/cm3, or any other numerical range, which is narrower, and which falls within such broader numerical range, as if such narrower numerical ranges were all expressly written herein.

In certain embodiments, the hydrophobic phase may be a non-toxic oil, such as non-toxic edible oil. In certain embodiments, the hydrophobic phase may include non-toxic edible oils, saturated or unsaturated fatty alcohols, aliphatic hydrocarbons, long chain triglycerides, fatty esters, and mixtures thereof. In certain embodiments, the hydrophobic phase may also comprise silicones, polysiloxanes, and mixtures thereof. In certain embodiments, the hydrophobic phase may be selected from mineral oil, in certain embodiments, petrolatum and mixtures thereof, more preferred petrolatum, e.g. white petrolatum, is used as the hydrophobic phase of the present composition. Examples of petrolatum include Snow White Pet—C from Calumet Specialty Products (Indianapolis, Ind.), G-2191 from Sonneborn (Parsippany, N.J.), G-2218 from Sonneborn, G-1958 from Sonneborn, G-2180 from Sonneborn, Snow White V28 EP from Sonneborn, and Snow White V30 from Sonneborn, G-2494 from Sonneborn, and mixtures thereof.

In certain embodiments, the multi-phase oral compositions may comprise petrolatum as a continuous phase. In certain embodiments, petrolatum is the continuous phase of the multi-phase oral compositions.

In certain embodiments, the aliphatic hydrocarbons may contain from about 10, 12, 14, or 16 to about 16, 18, 20, 22, 24, 26, 28, 30, 36, 40 carbon atoms such as decane, 2 ethyldecane, tetradecane, isotetradecane, hexadecane, eicosane, and mixtures thereof. In certain embodiments, long chain triglycerides may include vegetable oils, fish oils, animal fats, hydrogenated vegetable oils, partially hydrogenated vegetable oils, semi-synthetic triglycerides, synthetic triglycerides, and mixtures thereof. In certain embodiments, fractionated, refined or purified oils of these types can also be used. In certain embodiments, examples of long chain triglyceride-containing oils include almond oil; babassu oil; borage oil; black currant seed oil; canola oil; castor oil; coconut oil; corn oil; cottonseed oil; emu oil; evening primrose oil; flax seed oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; a mixture of hydrogenated cottonseed oil and hydrogenated castor oil; partially hydrogenated soybean oil; a mixture of partially hydrogenated soybean oil and partially hydrogenated cottonseed oil; glyceryl trioleate; glyceryl trilinoleate; glyceryl trilinolenate; a Q3-polyunsaturated fatty acid triglyceride containing oil; and mixtures thereof. The long chain triglyceride containing oils may be in certain embodiments selected from the group consisting of corn oil, olive oil, palm oil, peanut oil, safflower oil, sesame oil, soybean oil, castor oil, linseed oil, rape oil, rice bran oil, coconut oil, hydrogenated castor oil; partially hydrogenated soybean oil; glyceryl trioleate; glyceryl trilinoleate; a Q3-polyunsaturated fatty acid triglyceride containing oil; and mixtures thereof.

In certain embodiments, saturated or unsaturated fatty alcohols may have from about 6 to about 20 carbon atoms, cetearyl alcohol, lauryl alcohol, and mixtures thereof. For example, Lipowax (Cetearyl Alcohol and Ceteareth-20) are supplied and manufactured by Lipo Chemical. General information on silicones including silicone fluids, gums and resins, as well as the manufacture of silicones, can be found in Encyclopedia of Polymer Science and Engineering, Volume 15, Second Edition, pp 204-308, John Wiley & Sons Inc. 1989 and Chemistry and Technology of Silicones, Walter Noll, Academic Press Inc, (Harcourt Brue Javanovich, Publishers, New York), 1968, pp 282-287 and 409-426.

The multi-phase oral composition as disclosed herein may comprise additional ingredients, which can be added optionally, and which will be described below in further detail.

In certain embodiments, the multi-phase oral compositions of the present invention may not comprise a dispersant. In certain embodiments, a multi-phase oral composition, which may be in the form of an particles-in-semisolid dispersion may be formed even when no dispersant is used. Without being bound by a theory it is believed that the low amount of hydrophilic bleaching agent particles, combined with the rheological properties, flow properties, melting point or drop melting point, congealing point, and/or cone penetration consistency of the hydrophobic phase, and/or the process of preparation of the composition may help to disperse the hydrophilic bleaching agent particles into the hydrophobic phase and keep it dispersed even without the use of a dispersant. In certain embodiments, the multi-phase oral compositions may be substantially free of ingredients, for example a dispersant, especially dispersants with double or triple covalent bonds between adjacent carbon atoms that at temperatures (for example −7 C, 4 C, 23 C, 25 C, 30 C, 40 C, 50 C, or 60 C) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer 1) may compromise the efficacy, comfort, usage experience, concentration of actives or bleaching agents at the tooth surface over time, active or bleaching efficiency, or compatibility between ingredients, or 2) may react with other ingredients, degrade other ingredients, cause foam or pressure to build up, decrease the substantivity of the multi-phase oral composition to teeth, cause the multi-phase oral composition to thicken or harden, or make it difficult or impractical to manually dispense a suitable dose of the multi-phase oral composition from a tube, or cause one or more components of the multi-phase oral composition to macroscopically separate. "Substantially free of a dispersant" as understood herein means that the composition comprises less than 0.001% by weight of a dispersant. More preferred the present whitening multi-phase oral compositions are free of a dispersant, i.e. do not comprise any dispersant.

In certain embodiments, the multi-phase oral compositions may be substantially free of ingredients, for example water, hydrophilic liquids, glycerin, hydrophilic particles that become sticky when activated by moisture, hydroxy groups, or combinations thereof, that at temperatures (for example −7 C, 4 C, 23 C, 25 C, 30 C, 40 C, 50 C, or 60 C) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer 1) may compromise the efficacy, comfort, usage experience, concentration of actives or bleaching agents at the tooth surface over time, active or bleaching efficiency, or compatibility between ingredients, or 2) may react with other ingredients, degrade other ingredients, cause foam or pressure to build up, decrease the substantivity of the multi-phase oral composition to teeth, cause the multi-phase oral composition to thicken or harden, or make it difficult or impractical to manually dispense a suitable dose of the multi-phase oral composition from a tube, or cause one or more components of the multi-phase oral composition to macroscopically separate.

In certain embodiments, the present multi-phase oral compositions may comprise from 0 to about 0.1%, from about 0.1 to about 4%, from about 0.1 to about 3%, or from about 0.5% to about 1.5% by weight of the multi-phase oral composition, of water, hydrophilic liquids, glycerin, hydrophilic particles that become sticky when activated by moisture, or combinations thereof. In certain embodiments, the present multi-phase oral compositions may comprise less than about 0.001%, 0.01%, 0.1%, 0.2%, 0.5%, 1%, 2%, 3%, 4%, 5%, 10%, or 20% of water, hydrophilic liquids, glycerin, hydrophilic particles that become sticky when activated by moisture, or combinations thereof. In certain embodiments, the present multi-phase oral compositions may comprise 0% of water. In certain embodiments, the present multi-phase oral compositions are non-aqueous, substantially free of added water, or anhydrous.

In addition, in certain embodiments, the multi-phase oral compositions may be substantially free of ingredients with a strong odor for example alcohols, solvents, ethyl acetate, heptane, or ingredients with a boiling point less than 99 C. Without being bound by a theory it is believed that the decrease in surface tension produced by alcohol may decrease the retention time of the hydrophilic bleaching agent particles at the tooth surface, thereby decreasing the efficacy of the oral care actives. The presence of acids might contradict with the actives and/or may produce negative side effects as the tooth surface such as hypersensitivity etc. Thus, in certain embodiments, the present multi-phase oral compositions are preferably free of acids, free of alcohols, or free of a mixture thereof. In certain embodiments, multi-phase oral compositions may comprise less than 0.001% by weight of the composition, of acids and/or alcohols, preferably multi-phase oral compositions do not comprise acids and/or alcohols.

In certain embodiments, the hydrophobic phase of the multi-phase oral compositions may be substantially free of ingredients such as bleaching agents, that may react with other ingredients.

In certain embodiments, the multi-phase oral compositions may be substantially free of ingredients, for example fumed silica, sodium tripolyphosphate, polyorganosiloxanes, condensation products of silicone resins and iorganosiloxanes, polymers of styrene, polymers of ethylene, polymers of propylene, polyvinylpyrrolidone, glycerin, tin fluoride, or combinations thereof, that at temperatures (for example −7 C, 4 C, 23 C, 25 C, 30 C, 40 C, 50 C, or 60 C) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer 1) may compromise the efficacy, comfort, usage experience, concentration of actives or bleaching agents at the tooth surface over time, active or bleaching efficiency, or compatibility between ingredients, or 2) may react with other ingredients, degrade other ingredients, cause foam or pressure to build up, decrease the substantivity of the multi-phase oral composition to teeth, cause the multi-phase oral composition to thicken or harden, or make it difficult or impractical to manually dispense a suitable dose of the multi-phase oral composition from a tube, or cause one or more components of the multi-phase oral composition to macroscopically separate.

In certain embodiments, the multi-phase oral composition may be easy to manually dispense from a tube after 1 day, 2 days, 1 week, 2 weeks, 1 month, 2 months, 3 months, 6 months, 12 months, 18 months, or 24 months at −7 C, 4 C. 23 C. 25 C. 30 C. 40 C. 50 C, or 60 C.

Method Test to Determine if a Composition is Easy to Manually Dispense from a Tube
1. Select a foil laminate tube with the following dimensions:
    a. Total length from tip of nozzle to bottom of barrel: About 112 mm
    b. Internal diameter of barrel: About 28 mm
    c. Length of nozzle: About 21 mm
    d. Internal diameter of nozzle: About 9.7 mm for half the length of the nozzle attached to the barrel, and about 4.2 mm for the other half of the nozzle leading to the exit orifice of the nozzle.
2. Fill from about 35 to about 40 grams of the composition through the bottom of the barrel into the tube from step-1. Seal the bottom of the barrel using an ultrasonic sealer.
3. Allow the tube to stay undisturbed in a room or chamber in which the air is maintained at the temperature (for example −7 C, 4 C, 23 C, 25 C, 30 C, 40 C, 50 C, or 60 C) for the period of time after which the ease of dispensing is to be measured.
4. Allow the tube to equilibrate at about 23 C for at least a day.
5. Pick up the tube between the thumb and fingers of one hand. While holding the tube in the air, squeeze the tube firmly between the thumb and fingers for about 10 seconds. Measure the length of the bead of the composition dispensed out of the nozzle of the tube.
6. The composition is considered easy to dispense manually from a tube after the specified period of time at the specified temperature if at least 1 inch of product is dispensed in step-5.

In certain embodiments, the multi-phase oral composition may be substantially free of fumed silica since it may decrease the stability of the bleaching agent.

The Product Information document (Form No. 52-1052B-01, Aug. 9, 2016) from the supplier (Dow Corning Corporation) states that BIO-PSA Standard Silicone Adhesives are supplied using heptane or ethyl acetate as a solvent—both of which have a strong odor making them unappealing to use in the oral cavity. The European Chemicals Agency (March 2016) states that cyclic siloxane D4 is a persistent, bio-accumulative and toxic substance and cyclic siloxane D5 is a very persistent, very bio-accumulative substance.

In certain embodiments, the multi-phase oral compositions may be substantially free of ingredients, for example silicone adhesives, cyclic silicones, silicones, silicone fluids, dimethicone, paraffinum liquidum, mixtures of silicones with hydrocarbons, mixtures of liquid silicones with liquid hydrocarbons, trimethylsiloxysilicate/dimethiconol crosspolymers, or combinations thereof, that at temperatures (for example −7° C., 4° C., 23° C., 25° C., 30° C., 40° C., 50° C., or 60° C.) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer 1) may compromise the efficacy, comfort, usage experience, concentration of actives or bleaching agents at the tooth surface over time, active or bleaching efficiency, or compatibility between ingredients, or 2) may react with other ingredients, degrade other ingredients, cause foam or pressure to build up, decrease the substantivity of the multi-phase oral composition to teeth, cause the multi-phase oral composition to thicken or harden, or make it difficult or impractical to manually dispense a suitable dose of the multi-phase oral composition from a tube, or cause one or more components of the multi-phase oral composition to macroscopically separate.

In certain embodiments, the multi-phase oral compositions may be substantially free of ingredients, for example molecules with double or triple covalent bonds between adjacent carbon atoms, that at temperatures (for example −7° C., 4° C., 23° C., 25° C., 30° C., 40° C., 50° C., or 60° C.) and conditions that the multi-phase oral composition may be exposed to during manufacture, filling, shipping, or storage (for example 1 day, 2 days, 1 week, 2 weeks, 1 month, 2 months, 3 months, 6 months, 12 months, 18 months, or 24 months) prior to use by the consumer 1) may compromise the efficacy, comfort, usage experience, concentration of actives or bleaching agents at the tooth surface over time, active or bleaching efficiency, or compatibility between ingredients, or 2) may react with other ingredients, degrade other ingredients, cause foam or pressure to build up, decrease the substantivity of the multi-phase oral composition to teeth, build up, decrease the substantivity of the multi-phase oral composition to teeth, cause the multi-phase oral composition to thicken or harden, or make it difficult or impractical to manually dispense a suitable dose of the multi-phase oral composition from a tube, or cause one or more components of the multi-phase oral composition to macroscopically separate.

Thickening Agents, Viscosity Modifiers, or Particulate Fillers

The multi-phase oral compositions herein may comprise a safe and effective amount of a thickening agent, viscosity modifier or particulate fillers. A thickening agent may further provide acceptable rheology of the composition. The viscosity modifier may further function to inhibit settling and separation of components or control settling in a manner that facilitates re-dispersion and may control flow properties of the composition. In addition, a thickening agent or viscosity modifier may facilitate use of the present compositions with suitable applications devices, such as strips, films or dental trays by increasing the retention onto the surfaces of the application devices. The thickening agent, as described herein, may also serve as an adhesive.

When present a thickening agent, viscosity modifier, or particulate filler may be present at a level of from about 0.01% to about 99%, from about 0.1% to about 50%, from about 1% to about 25%, or from about 1% to about 10%, by weight of the multi-phase oral composition.

Suitable thickening agents, viscosity modifiers, or particulate fillers that can be used herein include organo modified clays, silicas, synthetic polymers such as crosslinked siloxanes, cellulose derivatives (e.g. methylcellulose, carboxymethylcellulose, hydroxyethylcellulose, hydroxypropylcellulose, hydroxy-propylmethylcellulose, etc.), carbomer polymers (e.g. crosslinked polyacrylic acid copolymer or homopolymer and copolymers of acrylic acid cross linked with a polyalkenyl polyether), natural and synthetic gums, karaya gum, guar gum, gelatin, algin, sodium alginate, tragacanth, chitosan, polyethylene oxide, acrylamide polymers, polyacrylic acid, polyvinyl alcohol, polyamines, polyquarternary compounds, ethylene oxide polymers, polyvinylpyrrolidone, cationic polyacrylamide polymers, waxes (which includes paraffin wax and microcrystalline waxes), polyethylene, fumed silica, polymethacrylates, olefin copolymers, hydrogenated styrene-diene copolymers, styrene polyesters, rubber, polyvinylchloride, nylon, fluorocarbon, polyurethane prepolymer, polyethylene, polystyrene, alkylated polystyrene, polypropylene, cellulosic resins, acrylic resins, elastomers, poly(n-butyl vinyl ether), poly(styrene-co-maleic anhydride), poly(alkyl fumarate co-vinyl acetate), poly(t-butyl styrene), and mixtures thereof.

Examples of polyethylene include A-C 1702 or A-C 6702 made by Honeywell Corp. (Morristown, N.J.), with a penetration value of about 98.5 and about 90.0, respectively, under ASTM D-1321; polyethylene Performalene series from Baker Hughes; this includes polyethylene Performalene 400 from Baker Hughes Inc. (Houston, Tex.). Examples of microcrystalline wax include the Multiwax series from Sonneborn (Parsippany, N.J.), Crompton (Witco); these include Multiwax 835, Multiwax 440, Multiwax 180, and mixtures thereof.

Examples of polymethacrylates include, for example, polyacrylate-co-methacrylate, polymethacrylate-co-styrene, or combinations thereof. Examples of elastomers include, for instance, hydrogenated styrene-co-butadiene, hydrogenated styrene-co-isoprene, ethylene-ethylene-propylene polymer, ethylene-propylene polymer, styrene-ethylene-ethylene-propylene-styrene polymer or combinations thereof. An example of a rubber includes hydrogenated polyisoprene. Other examples of viscosity modifiers can be found in "Chemistry and Technology of Lubricants," Chapman and Hall ($2^{nd}$ Ed. 1997).

Suitable carbomers comprises the class of homopolymers of acrylic acid crosslinked with an alkyl ether of pentaerythritol or an alkyl ether of sucrose. Carbomers are commercially available from B.F. Goodrich as the Carbopol® series, such as Carbopol 934, 940, 941, 956, and mixtures thereof. Homopolymers of polyacrylic acid are described, for example, in U.S. Pat. No. 2,798,053. Other examples of homopolymers which are useful include Ultrez 10, ETD 2050, and 974P polymers, which are available from The B.F.Goodrich Company (Greenville, S.C.). Such polymers are homopolymers of unsaturated, polymerizable carboxylic monomers such as acrylic acid, methacrylic acid, maleic acid, itaconic acid, maleic anhydride, and the like.

In certain embodiments, the multi-phase oral composition of the present invention and/or the hydrophobic phase of the present invention may be substantially free of structure-building agents, for example amphiphilic co-polymers such as polyvinylpyrrolidone-vinyl acetate, polyvinylpyrrolidone-co-polyvinyl butyrate, or polyvinylpyrrolidone-co-polyvinyl propionate co-polymers, that may not only thicken the oral care composition, but may also drive the oral care composition toward a homogenous state or maintain the oral care composition in a homogenous state. This is because structure-building agents such as amphiphilic co-polymers 1) have at least one monomer that is hydrophilic and this may make the multi-phase oral composition more susceptible to being washed away in saliva or other liquids, or 2) may drive the oral care composition toward a homogenous state and this may decrease the concentration of actives or bleaching agents at the tooth surface over time.

Optional Additional Oral Care Active Agents

The composition of the present invention may comprise a safe and effective amount of an additional oral care active agent, such as any material that is generally considered safe for use in the oral cavity and that provides changes to the overall appearance or health of the oral cavity. Suitable additional oral care actives include one or more anticalculus agent(s), fluoride ion source, antimicrobial agent(s), remineralization agent(s), dentinal desensitizing agent(s), anesthetic agent(s), antifungal agent(s), anti-inflammatory agent(s), selective H-2 antagonist(s), anticaries agent(s), nutrient(s), erythritol, probiotics, resolvins including eicosapentaenoic acid (EPA) and docosahexaenoic acid (DHA), as well as docosapentaenoic acid (DPA) clupanodonic acid, Resolvin D's RvD1 (7S,8R,17S-trihydroxy-DHA), RvD2 (7S,16R,17S-trihydroxy-DHA), RvD3 (4S,7R,17S-trihydroxy-DHA), RvD4 (4S,5,17S-trihydroxy-DHA), RvD5 (7S,17S-dihydroxy-DHA), and RvD6 (4S,17S-dihydroxy-DHA) and Resolvin E's: RvE1 (5S,12R,18R-trihydroxy-EPA), 18S-Rv1 (5S,12R,18S-trihydroxy-EPA), RvE2 (5S, 18R-dihydroxy-EPA), and RvE3 (17R,18R/S-dihydroxy-EPA), tranexamic acid, glycine, retinol, amino acids, niacinamide, human growth factors, and mixtures thereof. The additional oral care active agent may contain an active at a level where upon directed use, the benefit sought by the wearer is promoted without detriment to the oral surface to which it is applied. Examples of the oral conditions these actives address include, but, are not limited to, appearance and structural changes to teeth, stain removal, plaque removal, tartar removal, cavity prevention and treatment, inflamed and/or bleeding gums, mucosal wounds, lesions, ulcers, aphthous ulcers, cold sores, tooth abscesses, and the elimination of mouth malodor resulting from the conditions above and other causes, such as microbial proliferation. In certain embodiments, the level of the additional oral care active that may be used in the multi-phase oral compositions may be from about 0.01% to about 50%, from about 0.1% to about 20%, from about 0.5% to about 10%, or from about 1% to about 7%, by weight of the multi-phase oral composition or any other numerical range, which is narrower, and which falls within such broader numerical range, as if such narrower numerical ranges were all expressly written herein.

In certain embodiments, the additional oral care active agent may be a healing agent that promotes or enhances the healing or regenerative process. In certain embodiments, such healing agents may comprise hyaluronic acid or salts, glucosamine or salts, allantoin, curcumin, D panthenol, niacinamide, ellagic acid, flavanoids (including fisetin, querctin, luteolin, apigenin), vitamin E, ubiquinone, or mixtures thereof.

In certain embodiments, the additional oral care active agent may be one or more probiotics selected from *Lactobacillus reuteri* ATCC 55730; *Lactobacillus salivarius* strain TI12711 (LS 1); *Lactobacillus paracasei* ADP-1; *Streptococcus salivarius* K12; *Bifidobacterium* DN-173 010; Filtrate of *L. paracasei* strain (Pro-t-Action™); *S. Oralis* KJ3, *S. rattus* JH145, *S. uberis* KJ2; *Lactobacillus, reuteri* Prodentis; *Lactobacillus salivarius* LS1; *Lactobacillus paracasei*; *Lactobacillus paracasei* ADP1; *Streptococcus salivarius* M18, K12 or BLIS K12 and BLIS M18; *Bacillus Amyloliquefaciens*; *Bacillus Clausii*; *Bacillus Coagulans*; *Bacillus Subtilis*; *Bacillus subtilis*: E-300; *Bifidobacterium Animalis*; *Bifidobacterium* B6; *Bifidobacterium Bifidum*; *Bifidobacterium Breve* (Bb-03); *Bifidobacterium* DN-173 010; *Bifidobacterium* GBI 30 6068; *Bifidobacterium infantis*; *Bifidobacterium Lactis*; *Bifidobacterium lactis* Bb-12; *Bifidobacterium Longum*; *Bifido-* bacterium Thermophilum; Enterococcus Faecalis; Enterococcus Faecium; Enterococcus Faecium NCIMB 10415; Enterococcus LAB SF 68; Lactobacilli reuteri ATCC 55730 and ATCC PTA 5289; Lactobacilli reuteri ATCC 55730 and ATCC PTA 5289 (10:1); Lactobacillus Acidophilus; Lactobacillus acidophilus ATCC 4356 and Bifidobacterium bifidum ATCC 29521; Lactobacillus acidophilus; Bifidobacterium longum; Bifidobacterium bifidum; Bifidobacterium lactis; Lactobacillus Brevis; Lactobacillus Casei (subsp. Casi); Lactobacillus casei Shirota; Lactobacillus Confusus; Lactobacillus crispatus YIT 12319; Lactobacillus Curvatus; Lactobacillus Delbrueckii Ssp. Bulgaricus PXN 39; Lactobacillus Fermentum; Lactobacillus fermentum YIT 12320; Lactobacillus Gasseri; Lactobacillus gasseri YIT 12321; Lactobacillus Helveticus; Lactobacillus Johnsonii; Lactobacillus Kimchii; Lactobacillus Lactis L1A; Lactobacillus Paracasei (Lpc37); Lactobacillus paracasei GMNL-33; Lactobacillus Pentosus; Lactobacillus plantarum; Lactobacillus Plantarum; Lactobacillus Protectus; Lactobacillus Reuteri; Lactobacillus reuteri ATCC 55730; Lactobacillus reuteri SD2112 (ATCC55730); Lactobacillus Rhamnosus (GG); Lactobacillus rhamnosus GG; Lactobacillus rhamnosus GG; L. rhamnosus LC705; Propionibacterium freudenreichii ssp; shermanii JS; Lactobacillus rhamnosus L8020; Lactobacillus rhamnosus LB21; Lactobacillus Salivarius; Lactobacillus salivarius WB21; Lactobacillus Sporogenes; Lactococcus Lactis Ssp Diacetylactis; Lactococcus Lactis Ssp. Lactis; Pediococcus Acidilactici; Pediococcus Pentosaceus; Saccharomyces Boulardii; Saccharomyces Cerevisiae; Strep. uberis KJ2sm; Strep. oralis KJ3sm; trep. rattus JH145; Streptococcus mitis YIT 12322; Streptococcus Oralis KJ3; Streptococcus Rattus JH145; Streptococcus Salivarius (BLIS K12 or BLTS M18); Streptococcus salivarius K12; Streptococcus Thermophilus; Streptococcus Uberis KJ2; Thermus thermophiles; Weissella cibaria CMS2; Weissella cibaria CMS3; and Weissella cibaria CMU.

Probiotics can be used in the multi-phase oral compositions of the present invention to promote positive oral health effects, such as reduce caries and plaque, promote gum health, improve breath, and promote whitening. In certain embodiments, the efficacy of probiotics in the multi-phase oral compositions can be determined by measuring one or more of the following: reduction of the levels of salivary mutans streptococci; reduction of gingival crevicular fluid; reduction of periodontal pathogens (C. rectus and P. gingivitis) in subgingival plaque; decreased counts of yeast; decreased prevalence of oral candida; reduction of oral volatile sulfur compound (VSC) levels; and reduction of TNF-α and IL-8 production. Without being limited to theory it is believed that one or more of the above positive oral health effects may be achieved through the production of bacterial toxins, which remove or reduce certain types of bacteria in the oral cavity; further one or more of the above positive oral health effects may be achieved through bacterial production of one or more enzymes that inhibit the production of or dissolves/loosens biofilms or sticky deposits that can lead to oral health problems.

As the present multi-phase oral composition is directed to bleaching the tooth surface and removing or decreasing the stain attached thereto, in certain embodiments a safe and effective amount may be added of at least one anticalculus agent to the compositions as disclosed herein. In certain embodiments, said amount may be from about 0.01% to about 40%, from about 0.1% to about 25%, from about 4.5% to about 20%, or from about 5% to about 15%, by weight of the multi-phase oral composition or any other numerical range, which is narrower, and which falls within such broader numerical range, as if such narrower numerical ranges were all expressly written herein. The anticalculus agent may also be compatible with the other components of the multi-phase oral composition, in certain embodiments the whitening agent. The anticalculus agent may be selected from the group consisting of polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof, wherein the mentioned salts are usually alkali metal salts. In certain embodiments anticalculus agents used in the present multi-phase oral composition also show a stabilizing effect to the bleaching agents, such as pyrophosphates, polyphosphates, polyphophonates and mixtures thereof.

For example, the anticalculus agent may be a polyphosphate. A polyphosphate is generally understood to comprise two or more phosphate molecules arranged primarily in a linear configuration, although some cyclic derivatives may be present. Linear polyphosphates correspond to $(X\ PO_3)_n$ where n is about 2 to about 125, wherein preferably n is greater than 4, and X is for example sodium, potassium, etc. For $(X\ PO_3)_n$ when n is at least 3 the polyphosphates are glassy in character. Counter-ions for these phosphates may be the alkali metal, alkaline earth metal, ammonium, $C_2$-$C_6$ alkanolammonium and salt mixtures. Polyphosphates are generally employed as their wholly or partially neutralized water soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials, such as those manufactured by FMC Corporation which are commercially known as Sodaphos (n=6), Hexaphos (n=13), Glass H (n=21), and mixtures thereof. If present, the present compositions will typically comprise from about 0.5% to about 20%, in certain embodiments from about 4% to about 15%, more particular from about 6% to about 12%, by weight of the composition of polyphosphate.

The pyrophosphate salts useful in the present compositions include, alkali metal pyrophosphates, di-, tri-, and mono-potassium or sodium pyrophosphates, dialkali metal pyrophosphate salts, tetraalkali metal pyrophosphate salts, and mixtures thereof. For example, the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof, wherein tetrasodium pyrophosphate is preferred. Tetrasodium pyrophosphate may be the anhydrous salt form or the decahydrate form, or any other species stable in solid form in the present compositions. The salt is in its solid particle form, which may be its crystalline and/or amorphous state, with the particle size of the salt preferably being small enough to be aesthetically acceptable and readily soluble during use. The level of pyrophosphate salt in the present compositions may be from about 1.5% to about 15%, in certain embodiments from about 2% to about 10%, and more particular from about 3% to about 8%, by weight of the composition.

The phosphate sources, including but are not limited to, polyphosphates and pyrophosphates, are described in more detail in Kirk & Othmer, *Encyclopedia of Chemical Technology*, Fourth Edition, Volume 18, Wiley-Interscience Publishers (1996), pages 685-707, incorporated herein by reference in its entirety, including all references incorporated into Kirk & Othmer.

Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof (such as those which the alkane moiety has five, six or seven carbon atoms, in which the nitrogen atom is unsubstituted or carries a lower alkyl substitutent, e.g. methyl), azacyclohexane-2,2-diphosphonic acid, azacyclopentane-2,2-diphosphonic acid, N-methyl-azacyclopentane-2,3-diphosphonic acid, EHDP (ethanehydroxy-1,1,-diphosphonic acid), AHP (azacycloheptane-2,2-diphosphonic acid, a.k.a. 1-azocycloheptylidene-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts.

In addition, antimicrobial antiplaque agents may also be present in the present compositions. Such agents may include, but are not limited to, triclosan, hops acids from hops extracts, such as hops alpha acids, including, humulone, adhumulone, cohumulone, posthumulone, prehumulon, and combinations thereof, or hops beta acids, including, lupulone, adlupulone, colupulone, and combinations thereof, 5-chloro-2-(2,4-dichlorophenoxy)-phenol, as described in The Merck Index, 11th ed. (1989), pp. 1529 (entry no. 9573) in U.S. Pat. No. 3,506,720, and in European Patent Application No. 0,251,591; chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; cocomidyl propyl betaine, sodium cocomidyl glutamate, sodium lauryl sarcosinate, GTF inhibitors, povidone iodine delmopinol, propolis, phthalic acid and its salts, monoperthalic acid and its salts and esters, ascorbyl stearale, oleoyl saicosine, alkyl sulfate. In addition, there may be effective antimicrobial amounts of essential oils, herbal extracts, and combinations thereof for example citral, geranial, rosemary extract, tea extract, *magnolia* extract, eucalyptol geraniol. carvacrol, citral, hinokitol. catechol, methyl salicylate, epigallocatechin gallate, epigallocatechin. gallic acid, miswak extract, sea-buckthorn extract, and combinations of menthol, eucalyptol, thymol and methyl salicylate; antimicrobial metals and salts thereof for example those providing zinc ions, stannous ions, copper ions, and/or mixtures thereof; bisbiguanides, or phenolics; antibiotics such as augmentin, amoxicillin, tetracycline, doxycycline, minocycline, and metronidazole; and analogs and salts of the above antimicrobial antiplaque agents and/or anti-fungals such as those for the treatment of *Candida albicans*. If present, these agents generally are present in a safe and effective amount for example from about 0.1% to about 5% by weight of the present compositions.

The present composition may comprise a safe and effective amount of an anticaries agent, and mixtures thereof. The anticaries agent may be selected from the group consisting of fluoride, sodium fluoride, potassium fluoride, titanium fluoride, hydrofluoric acid, amine fluoride, sodium monofluorophosphate, ammonium fluoride, stannous fluoride, stannous chloride, stannous gluconate, copper salts, copper chloride, copper glycinate, zinc chloride, zinc lactate, zinc citrate, zinc phosphate, ssodium iodide, potassium iodide, calcium chloride, calcium lactate, calcium phosphate, hydroxyapatite, fluoroapatite, amorphous calcium phosphate, crystalline calcium phosphate, sodium bicarbonate, sodium carbonate, calcium carbonate, oxalic acid, dipotassium oxalate, monosodium monopotassium oxalate, casein phosphopeptides, casein phosphopeptide coated hydroxy apatite, bioglass containing one or more of $SiO_2$, CaO, $Na_2O$, $P_2O$, $CaF_2$, $B_2O_3$, $K_2O$, MgO, such as those disclosed in U.S. Pat. No. 5,735,942. In certain embodiments, the instant compositions provide from about 50 ppm to 10,000 ppm, more preferably from about 100 to 3000 ppm, of fluoride ions in the compositions that contact dental surfaces when used with the composition as disclosed herein.

Coolants, desensitizing agents and numbing agents can be used as optional ingredients in compositions of the present invention, in certain embodiments at a level of from about 0.001% to about 10%, more particular from about 0.1% to about 1%, by weight of the composition. Coolants, desensitizing agents and numbing agents may decrease potential negative perceptions, such as tingling, burning etc. . . . . Coolant can be any of a wide variety of materials. Included among such materials are carboxamides, menthol, ketals, diols, and mixtures thereof. Optional coolants in the present compositions may be the paramenthan carboxyamide agents such as N-ethyl-p-menthan-3-carboxamide (known as "WS-3"), N,2,3-trimethyl-2-isopropylbutanamide (known as "WS-23"), menthol, 3-1-menthoxypropane-1,2-diol (known as TK-10), menthone glycerol acetal (known as MGA) menthyl lactate (known as Frescolat®), and mixtures thereof. The terms menthol and menthyl as used herein include dextro- and levorotatory isomers of these compounds and racemic mixtures thereof. Desensitizing or Antipain agent may include, but are not limited to, strontium chloride, potassium nitrate, natural herbs such as gall nut, *Asarum*, Cubebin, Galanga, scutellaria, Liangmianzhen, Baizhi, etc. Suitable numbing agents include benzocaine, lidocaine, clove bud oil, and ethanol.

In addition, anti-inflammatory agents may be present in the multi-phase oral compositions as disclosed herein. Such agents may include, but are not limited to, non-steroidal anti-inflammatory agents such as aspirin, ketorolac, flurbiprofen, ibuprofen, naproxen, indomethacin, acetaminophen, acetyl salyscylic acid, steroids, ketorolac, naproxen, ketoprofen, piroxicam and meclofenamic acid, COX-2 inhibitors such as valdecoxib, celecoxib and rofecoxib, and mixtures thereof. If present, the anti-inflammatory agents generally comprise from about 0.001% to about 5% by weight of the compositions.

In addition, nutrients, such as minerals, may improve the teeth and the tooth surface and thus can be included with the compositions as disclosed herein. Suitable minerals are e.g. calcium, phosphorus, fluoride, zinc, manganese, potassium and mixtures thereof. These minerals are e.g disclosed in Drug Facts and Comparisons (loose leaf drug information service), Wolters Kluer Company, St. Louis, Mo., ©1997, pp 10-17.

In addition, the compositions as disclosed herein may optionally comprise a safe and effective amount of a flavoring agent. Suitable flavoring agents include oil of wintergreen, oil of peppermint, oil of spearmint, clove bud oil, menthol, anethole, methyl salicylate, eucalyptol, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal (known as CGA), and mixtures thereof. If present the flavoring agents are generally used at levels of from about 0.01% to about 30%, in certain embodiments from about 1% to about 20%, more particular from about 1.5% to about 15%, by weight of the composition.

In addition, the present compositions may optionally comprise sweetening agents including sucralose, sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. If present, the composition contains from about 0.1% to about 10% of these agents, in certain embodiments from about 0.1% to about 1%, by weight of the composition.

In addition, dyes, pigments, colorants, and mixtures thereof may optionally be included in the present composition to give the compositions herein colored appearance. An advantage of adding pigments and/or colorants to the compositions herein is that it will allow the user to see if the composition covers their teeth evenly and completely, since coverage is easier to see with a colored composition. In addition, the colorant may provide color similar to the color of bleached teeth. Colorants useful herein are stable with the bleach agent and are those recognized as safe. The levels of dye, pigments and colorants that are optionally used herein are in the range of about 0.05% to about 20%, in certain embodiments from about 0.10% to about 15% and more particular from about 0.25% to about 5% by weight of the composition.

In certain embodiments of the present invention, it has been surprisingly found that two or more oral care active agents that are normally incompatible with each other can be combined in the same composition. For example, in certain embodiments, the present invention may comprise hydrophilic bleaching agent particles combined with an additional oral care active agent that further improves the bleaching efficacy of the composition. Examples of such embodiments include hydrophilic bleaching agent particles combined with additional oral care actives that may provide a driving force to increase the pH when contacted with water. Specifically, examples of such embodiments include hydrophilic bleaching agent particles comprising peroxides combined with sodium bicarbonate (baking soda). It is worth noting that U.S. Pat. No. 5,814,303 states: "When in contact, peroxide and baking soda are reactive towards one another. Therefore these ingredients must be maintained separately until time of use. Dispensing packages have been developed which physically isolate peroxide and baking soda by separating them into different compartments.". It has now been surprisingly found that in certain embodiments of the present invention, peroxide and baking soda can in fact be combined in the same composition eliminating the need for different compartments. While not wishing to be bound by theory: It is hypothesized that in certain embodiments of the present invention, dispersing particles of two or more hydrophilic oral care active agents that are normally incompatible with each other in a hydrophobic phase keeps the particles substantially separated from each other with hydrophobic phase between the particles—this separation even on a microscopic scale, may minimize or eliminate the incompatibility. Furthermore, it is hypothesized that when particles of one of the hydrophilic oral care agents come in contact with moisture, for example at the time of use in the oral cavity, the components of the particles may at least partially dissolve or swell and make direct contact with components of the particles of the other oral care agents; however, this may happen primarily at the time of use in the oral cavity, and only minimally or not at all prior to that in the composition. Thus, in certain embodiments, the multi-phase oral composition of the present invention may comprise two or more oral care active agents that are normally incompatible with each other.

Bleaching Efficacy

In certain embodiments, the bleaching efficacy of the present invention, as measured per the clinical protocol disclosed herein and calculated as $-\Delta b^*$ may be at least about, 0.25, 0.5, 1, 1.5, 2, 2.5, 3, 4, 5, 6, 7, 8, 9 or 10 or any other numerical range, which is narrower and which falls within such broader numerical range, as if such narrower numerical ranges were all expressly written herein.

In certain embodiments, the bleaching efficacy of the present invention, as measured per the clinical protocol disclosed herein, and calculated as $-\Delta b^*$ may be at least about 0.25, preferably at least about 0.5, more preferred at least about 1.0, even more preferred at least about 1.5, even more preferred at least about 2, even more preferred at least about 2.5, even more preferred at least about 3, even more preferred at least about 3.5, and even more preferred at least about 4, or any other numerical range, which is narrower and which falls within such broader numerical range, as if such narrower numerical ranges were all expressly written herein. Generally, a change in yellowness, as measured per the clinical protocol as disclosed herein, and calculated as $-\Delta b^*$ of at least 0.25 is noticeable.

The present invention may deliver a surprisingly high ratio of bleaching efficacy of the present invention, as measured per the clinical protocol disclosed herein, and calculated as $-\Delta b^*$, to the weight percent of bleaching agent present in the overall multi-phase oral composition. For example, a $-\Delta b^*$ of 1.5 with a composition containing 3% of bleaching agent, would deliver a ratio of bleaching efficacy, as measured per the clinical protocol as disclosed herein, and calculated as $-\Delta b^*$, to the weight percent of bleaching agent present in the overall multi-phase oral composition of 0.5.

In certain embodiments, the ratio of bleaching efficacy of the present invention, as measured per the clinical protocol disclosed herein, and calculated as $-\Delta b^*$ to the weight percent of bleaching agent present in the overall multi-phase oral composition may be at least about, 0.25, 0.5, 1, 1.5, 2, 2.5, 5, 10, or 15 or any other numerical range, which is narrower and which falls within such broader numerical range, as if such narrower numerical ranges were all expressly written herein.

In certain embodiments, the ratio of bleaching efficacy of the present invention, as measured per the clinical protocol disclosed herein, and calculated as $-\Delta b^*$ to the weight percent of bleaching agent present in the overall multi-phase oral composition may be at least about 2.5, preferably at least about 5, more preferred at least about 10, even more preferred at least about 15.

In certain embodiments, the bleaching efficacy of the present invention, as measured per the clinical protocol disclosed herein and calculated as $-\Delta b^*$ may be at least about 10%, at least about 100%, at least about 1000%, or at least about 10,000% more than the bleaching efficacy of a comparative oral care composition in the form of an aqueous solution or aqueous gel. The comparative oral care composition comprises the same bleaching agent at the same overall concentration dissolved into the aqueous solution or aqueous gel.

The present invention may deliver: 1) a surprisingly high ratio of bleaching efficacy, as measured per the clinical protocol as disclosed herein, and calculated as $-\Delta b^*$, to the fraction of participants who reported oral irritation or were observed to have oral irritation that was possibly or probably attributed to the composition tested; 2) a surprisingly high ratio of bleaching efficacy of the present invention, as measured per the clinical protocol as disclosed herein, and calculated as $-\Delta b^*$. treatments to the fraction of participants who reported tooth sensitivity that was possibly or probably attributed to the composition; or 3) a surprisingly high ratio of bleaching efficacy of the present invention, as measured per the clinical protocol as disclosed herein, and calculated as $-\Delta b^*$, to the fraction of participants who reported tooth sensitivity or reported oral irritation or were observed to have oral irritation that was possibly or probably attributed to the composition.

In certain embodiments, the ratio of bleaching efficacy of the present invention, as measured per the clinical protocol as disclosed herein, and calculated as $-\Delta b^*$, to the fraction of participants who report tooth sensitivity that is possibly or probably attributed to the present invention may be at least about 6, 7, 8, 9, 10, 15, 20, 25, 50, or 100 or any other numerical range, which is narrower and which falls within such broader numerical range, as if such narrower numerical ranges were all expressly written herein.

In certain embodiments, the ratio of bleaching efficacy of the present invention, as measured per the clinical protocol as disclosed herein, and calculated as $-\Delta b^*$, to the fraction of participants who report tooth sensitivity that is possibly or probably attributed to the present invention may be at least about 6, preferably at least about 7, more preferred at least about 8, even more preferred at least about 9, even more preferred at least about 10, even more preferred at least about 15, even more preferred at least about 20, even more preferred at least about 25, and even more preferred at least about 50, or any other numerical range, which is narrower and which falls within such broader numerical range, as if such narrower numerical ranges were all expressly written herein.

In certain embodiments, the ratio of bleaching efficacy of the present invention, as measured per the clinical protocol as disclosed herein, and calculated as $-\Delta b^*$, to the fraction of participants who report oral irritation or are observed to have oral irritation that is possibly or probably attributed to the present invention may be at least about 6, 7, 8, 9, 10, 15, 20, 25, 50, or 100 or any other numerical range, which is narrower and which falls within such broader numerical range, as if such narrower numerical ranges were all expressly written herein.

In certain embodiments, the ratio of bleaching efficacy of the present invention, as measured per the clinical protocol as disclosed herein, and calculated as $-\Delta b^*$, to the fraction of participants who report oral irritation or are observed to have oral irritation that is possibly or probably attributed to the present invention may be at least about 6, preferably at least about 7, more preferred at least about 8, even more preferred at least about 9, even more preferred at least about 10, even more preferred at least about 15, even more preferred at least about 20, even more preferred at least about 25, and even more preferred at least about 50, or any other numerical range, which is narrower and which falls within such broader numerical range, as if such narrower numerical ranges were all expressly written herein.

In certain embodiments, the ratio of bleaching efficacy of the present invention, as measured per the clinical protocol as disclosed herein, and calculated as $-\Delta b^*$, to the fraction of participants who report tooth sensitivity or report oral irritation or are observed to have oral irritation that is possibly or probably attributed to the present invention may be at least about 6, 7, 8, 9, 10, 15, 20, 25, 50, or 100 or any other numerical range, which is narrower and which falls within such broader numerical range, as if such narrower numerical ranges were all expressly written herein.

In certain embodiments, the ratio of bleaching efficacy of the present invention, as measured per the clinical protocol as disclosed herein, and calculated as $-\Delta b^*$, to the fraction of participants who report tooth sensitivity or report oral irritation or are observed to have oral irritation that is possibly or probably attributed to the present invention may be at least about 6, preferably at least about 7, more preferred at least about 8, even more preferred at least about 9, even more preferred at least about 10, even more preferred at least about 15, even more preferred at least about 20, even more preferred at least about 25, and even more preferred at least about 50, or any other numerical range, which is narrower and which falls within such broader numerical range, as if such narrower numerical ranges were all expressly written herein.

Clinical Protocol

The bleaching efficacies of the multi-phase oral compositions are measured using the following clinical protocol. Per treatment group, 17 to 25 participants are recruited to complete the clinical study when testing compositions with less than about 1% bleaching agent, and 8 to 25 participants when testing compositions with at least about 1% bleaching agent. Recruited participants must have four natural maxillary incisors with all measurable facial sites. The mean baseline L* of the group of participants must be from 71 to 76, and the mean baseline b* of the group of participants must be from 13 to 18. In addition, participants with malocclusion on maxillary anterior teeth, severe or atypical intrinsic staining, such as that caused by tetracycline, fluorosis or hypo-calcification, dental crowns or restorations on the facial surfaces of maxillary anterior teeth, self-reported medical history of melanoma, current smoking or tobacco use, light-sensitivity or a pigmentation skin disorder, self-reported tooth sensitivity, or previous tooth whitening using a professional treatment, over-the-counter kit, or investigational product, are excluded from the study. Participants are provided with take-home kits with Crest Cavity Protection toothpaste and Oral-B Indicator soft manual toothbrush (both from Procter & Gamble, Cincinnati, Ohio, USA) to be used twice a day in the customary manner.

The participants use a toothbrush ("Anchor 41 tuft white toothbrush" from Team Technologies, Inc. Morristown, Tenn., USA) to brush their teeth with water for 30 seconds prior to being treated with the multi-phase oral composition. The maxillary anterior teeth of each participant are treated with the multi-phase oral composition for 60 minutes once daily using a strip of polyethylene as a delivery carrier. The polyethylene strips are 66 mm×15 mm in size and 0.0178 mm thick. From 0.6 g to 0.8 g of the multi-phase oral composition is applied across each strip of polyethylene prior to applying to the maxillary anterior teeth.

Figure 6:
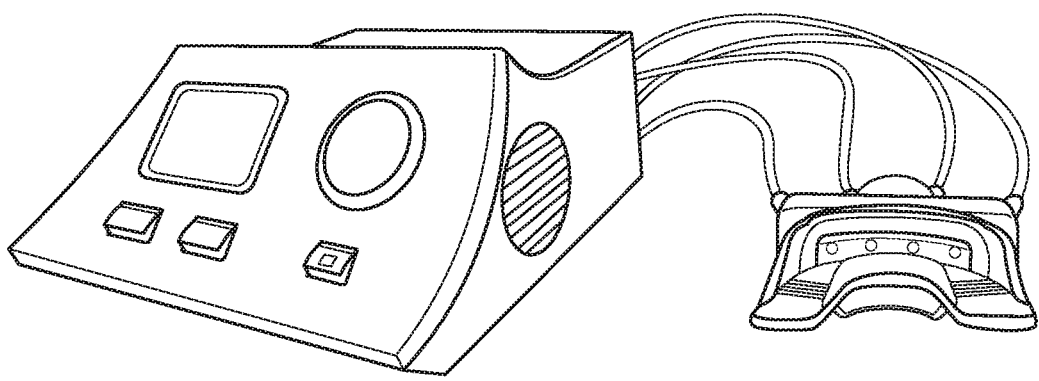
FIG. 6 shows a device for delivering electromagnetic radiation with a peak intensity wavelength of about 455 nm to a transparent mouthpiece to help position the electromagnetic radiation reproducibly toward the tooth surface; according to certain embodiments of the present invention.

If the multi-phase oral composition is used with electromagnetic radiation:
1) After 50 minutes of treatment with the multi-phase oral composition on the strip, the electromagnetic radiation is applied toward the facial surfaces of the maxillary anterior teeth for 10 minutes,
2) The electromagnetic radiation is directed toward the maxillary anterior teeth through the strip and through the multi-phase oral composition,
3) The strip needs to allow at least about 90% of the electromagnetic radiation from 400 nm to 500 nm to pass through, and
4) The electromagnetic radiation is delivered via four fiber-optic cables (model number M71L01 from Thorlabs, Newton, N.J., USA) connected to four high power LEDs with a peak intensity wavelength of 455 nm (model number M455F1 from Thorlabs, Newton, N.J., USA) as shown in FIG. 6. The four LEDs are run at 1000 mA each using an LED Driver and Hub (model numbers DC4104 and DC4100-HUB from Thorlabs, Newton, N.J., USA). The exit ends of the four fiber-optic cables are mounted behind a transparent mouthpiece to help position the electromagnetic radiation reproducibly against the outer surface of the strip. The exit ends of the four fiber-optic cables are about 7 mm away from the exit surface of the mouthpiece with the electromagnetic radiation passing through the transparent mouthpiece. The bite-shelf of the mouthpiece is offset such that the transparent window through which the electromagnetic radiation passes toward the maxillary anterior teeth is 7.4 mm high. Also, the transparent window through which the electromagnetic radiation passes toward the maxillary anterior teeth is 40 mm long measured linearly from end to end (not including the curvature). The exit ends of the fiber-optic cables are positioned and angled such that the cones of electromagnetic radiation exiting from the fiber-optic cables are centered within the transparent window through which the electromagnetic radiation passes toward the maxillary anterior teeth as shown in FIG. 6. Also, the exit ends of the four fiber-optic cables are spaced such that the cones of electromagnetic radiation are spaced across the length of the transparent window through which the electromagnetic radiation passes toward the maxillary anterior teeth as shown in FIG. 6. The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth needs to be from about 175 mW/cm$^2$ to about 225 mW/cm$^2$ as measured by the method disclosed herein.

Once 60 minutes of the treatment with the multi-phase oral composition is completed, the strip is removed. This treatment is applied once daily for a minimum of 7 days for compositions with less than about 1% bleaching agent, and a minimum of 3 days for compositions with at least about 1% bleaching agent.

The change in tooth color due to the treatment with the multi-phase oral composition is measured using the procedure described below the day after the 7' treatment for compositions with less than about 1% bleaching agent and after the 3$^{rd}$ treatment for compositions with at least about 1% bleaching agent.

Tooth color is measured using a digital camera having a lens equipped with a polarizer filter (Camera model no. CANON EOS 70D from Canon Inc., Melville, N.Y. with NIKON 55 mm micro-NIKKOR lens with adapter). The light system is provided by Dedo lights (model number DLH2) equipped with 150 watt, 24V bulbs model number (Xenophot model number HL X64640), positioned about 30 cm apart (measured from the center of the external circular surface of one of the glass lens through which the light exits to the other) and aimed at a 45 degree angle, such that the light paths intersect at the vertical plane of the chin rest about 36 cm in front of the focal plane of the camera. Each light has a polarizing filter (Lee 201 filter), and a cutoff filter (Rosco 7 mil Thermashield filter from Rosco, Stamford, Conn., USA).

At the intersection of the light paths, a fixed chin rest is mounted for reproducible repositioning in the light field. The camera is placed between the two lights such that its focal plane is about 36 cm from the vertical plane of the chin rest. Prior to beginning the measurement of tooth color, color standards are imaged to establish calibration set-points. A Munsell N8 grey standard is imaged first. The white balance of the camera is adjusted, such that the RGB values of grey are 200. Color standards are imaged to get standard RGB values of the color chips. The color standards and grey standard are listed below (from Munsell Color, Division of X-rite, Grand Rapids, Mich., USA). Each color standard is labeled with the Munsell nomenclature. To create a grid of color standards they can be arranged in the following manner. This enables multiple color standards to be contained in a single image captured of the grid of color standards.

Color Standard Grid 1

| | | | | | |
|---|---|---|---|---|---|
| 7.5R 6 8 | 2.5R 6 10 | 10YR 6.5 3 | POLARIZATION CHECK | 5R 7 8 | N 3.5 0 |
| 7.5RP 6 6 | 10R 5 8 | 5YR 7 3 | 2.5Y 8.5 2 | 2.2YR 6.47 4.1 | 7.5YR 7 4 |
| 5YR 8 2 | N 8 0 | 10R 7 4 | N 8 0 | 5YR 7.5 2.5 | 2.5Y 8 4 |
| 5YR 7 3.5 | 5YR 7 2.5 | 5YR 5 2 | 5YR 7.5 2 | N 6.5 0 | N 9.5 0 |

Color Standard Grid 2

| | | | | | |
|---|---|---|---|---|---|
| 5YR 7.5 3.5 | 2.5Y 6 4 | 10YR 7.5 3.5 | 2.5R 7 8 | 7.5R 7 8 | 10YR 7.5 2 |
| 10YR 7.5 2.5 | N 5 0 | 2.5R 6 8 | 10YR 7 2 | 5R 7 4 | 10YR 7 2.5 |
| N 6.5 0 | 7.5RP 6 8 | 7.5R 8 4 | 5Y 8 1 | 7.5YR 8 2 | 2.2YR 6.47 4.1 |
| N 5 0 | 2.5Y 8 4 | 10YR 7 3 | N 9.5 0 | 10RP 7 4 | 2.5Y 7 2 |

Color Standard Grid 3

| | | | | | | |
|---|---|---|---|---|---|---|
| 5R 6 10 | N 8.5 0 | 10YR 6.5 3.5 | 10RP 6 10 | N 8 0 | | 7.5YR 7 3 |
| 2.5Y 3.5 0 | 10YR 7 3.5 | 5Y 8.5 1 | 5YR 8 2.5 | 5YR 7.5 3 | | 5R 5 6 |
| 10YR 7.5 3 | 5YR 6.5 3.5 | 2.5YR 5 4 | 2.5Y 8 2 | 10YR 8 2 | | 2.5Y 7 2 |
| 2.5R 6 6 | 5R 7 6 | 10YR 8 2.5 | 10R 5 6 | N 6.5 0 | | 7.5YR 8 3 |

For baseline tooth color, participants use a toothbrush ("Anchor 41 tuft white toothbrush" from Team Technologies, Inc. Morristown, Tenn., USA) to brush their teeth with water to remove debris from their teeth. Each participant then uses cheek retractors (from Washington Scientific Camera Company, Sumner, Wash., USA; treated with at frosted matte finish at A&B Deburring Company, Cincinnati, Ohio, USA) to pull the cheeks back and allow the facial surfaces of their teeth to be illuminated. Each participant is instructed to bite their teeth together such that the incisal edges of the maxillary incisors contact the incisal edges of the mandibular incisors. The participants are then positioned on the chin rest at the intersection of the light paths in the center of the camera view and the tooth images are captured. After all participants are imaged, the images are processed using image analysis software (Optimas manufactured by Media Cybernetics, Inc. of Silver Spring, Md.). The central four incisors are isolated and the average RGB values of the teeth are extracted.

After the participants have used a whitening product, but prior to capturing participant's tooth images, the system is set to the baseline configuration and calibrated as previously discussed. After calibration, each participant is imaged a second time using the same procedure as before making sure the participant is in the same physical position as the pre-treatment image including orientation of the teeth. The images are processed using the image analysis software to obtain the average RGB values of the central four maxillary incisors. The RGB values of all of the images are then mapped into CIE $L^{*'}a^{*}b^{*}$ color space using the RGB values and the $L^{*}a^{*}b^{*}$ values of the color chips on the color standard. The $L^{*}a^{*}b^{*}$ values of the color chips on the color standard are measured using a Photo Research SpectraScan PR650 from Photo Research Inc., LA using the same lighting conditions described for capturing digital images of the facial dentition. The PR650 is positioned the same distance from the color standards as the camera. Each chip is individually measured for $L^{*}a^{*}b^{*}$ after calibration according to the manufacturer's instructions. The RGB values are then transformed into $L^{*}a^{*}b^{*}$ values using regression equations such as:

$$L^{*}=25.16+12.02^{*}(R/100)+11.75^{*}(G/100)-2.75^{*}(B/100)+1.95^{*}(G/100)^{3}$$

$$a^{*}=-2.65+59.22^{*}(R/100)-50.52^{*}(G/100)+0.20^{*}(B/100)-29.87^{*}(R/100)^{2}+20.73^{*}(G/100)^{2}+8.14^{*}(R/100)^{3}-9.17^{*}(G/100)^{3}+3.64^{*}[(B/100)^{2}]^{*}[R/100]$$

$$b^{*}=-0.70+37.04^{*}(R/100)+12.65^{*}(G/100)-53.81^{*}(B/100)-18.14^{*}(R/100)^{2}+23.16^{*}(G/100)^{*}(B/100)+4.70^{*}(R/100)^{3}-6.45^{*}(B/100)^{3}$$

The $R^{2}$ for $L^{*}$, $a^{*}$, and $b^{*}$ should be >0.95. Each study should have its own equations.

These equations are generally valid transformations in the area of tooth color ($60<L^{*}<95$, $0<a^{*}<14$, $6<b^{*}<25$). The data from each participant's set of images is then used to calculate product whitening performance in terms of changes in $L^{*}$, $a^{*}$ and $b^{*}$—a standard method used for assessing whitening benefits. When evaluating compositions with less than about 1% bleaching agent: Changes in $L^{*}$ is defined as $\Delta L^{*}=L^{*}_{day\ after\ 7\ treatments}-L^{*}_{baseline}$ where a positive change indicates improvement in brightness; Changes in $a^{*}$ (red-green balance) is defined as $\Delta a^{*}=a^{*}_{day\ after\ 7\ treatments}-a^{*}_{baseline}$ where a negative change indicates teeth which are less red; Changes in $b^{*}$ (yellow-blue balance) is defined as $\Delta b^{*}=b^{*}_{day\ after\ 7\ treatments}-b^{*}_{baseline}$ where a negative change indicates teeth are becoming less yellow. When evaluating compositions with at least about 1% bleaching agent: Changes in $L^{*}$ is defined as $\Delta L^{*}=L^{*}_{after\ 3\ treatments}-L^{*}_{baseline}$ where a positive change indicates improvement in brightness; Changes in $a^{*}$ (red-green balance) is defined as $\Delta a^{*}=a^{*}_{after\ 3\ treatments}-a^{*}_{baseline}$ where a negative change indicates teeth which are less red; Changes in $b^{*}$ (yellow-blue balance) is defined as $\Delta b^{*}=b^{*}_{after\ 3\ treatments}-b^{*}_{baseline}$ where a negative change indicates teeth are becoming less yellow. $-\Delta b^{*}$ is used as the primary measure of bleaching efficacy. The overall color change is calculated by the equation $\Delta E=(\Delta L^{*2}+\Delta a^{*2}+\Delta b^{*2})^{1/2}$.

After using the whitening products, color changes in CIE Lab color space can be calculated for each participant based on the equations given.

To validate the above clinical protocol, the bleaching efficacy (calculated as $-\Delta b^{*}$) of the validation composition specified below (delivered on a strip and used with electromagnetic radiation as disclosed herein) needs to be measured the day after the $7^{th}$ treatment and demonstrated to be >0.5.

| VALIDATION COMPOSITION FOR CLINICAL PROTOCOL | (Wt %) |
|---|---|
| 35% aqueous solution $H_2O_2$[1] | 0.2857 |
| Petrolatum[2] | 99.7143 |
| total | 100.00 |
| % $H_2O_2$ in total oral compos. | 0.099995 |
| RATIO* | 350.02 |

*RATIO of the concentration in weight percent of $H_2O_2$ present in the aqueous phase to the concentration in weight percent of $H_2O_2$ present in the overall composition
[1] ultra Cosmetic Grade from Solvay, Houston, Texas
[2] G-2191 Grade from Sonneborn, LLC., Parsippany, NJ Procedure to Make the Validation Composition for Clinical Protocol A 500 gram batch of the validation composition is made by weighing the aqueous solution of hydrogen peroxide ($H_2O_2$) and petrolatum into a Speedmixer container ("Max 300 Long Cup Translucent", item number 501 218t from Flacktek Inc., Landrum, S.C.), and mixing in a Speedmixer at 800 RPM for 5 seconds, 1200 RPM for 5 seconds, and 1950 RPM for 2 minutes. The walls of the container are then scraped down with a plastic spatula, and the contents are mixed a second time at 800 RPM for 5 seconds, 1200 RPM for 5 seconds, and 1950 RPM for 2 minutes. The walls of the container are then scraped down with a plastic spatula, and the contents are mixed a third time at 800 RPM for 5 seconds, 1200 RPM for 5 seconds, and 1950 RPM for 2 minutes.

Optional Application Systems

In addition, the present invention may further relate to a delivery system for delivering the present compositions to the tooth surface. For example, in certain embodiments the compositions of the present invention may deliver whitening benefits to the oral cavity by being directly applied to the teeth without using a delivery carrier system. In addition, in certain embodiments the present invention may include a delivery system comprising the present compositions in combination with a delivery carrier. For example, the delivery system may comprise a first layer of a carrier material and a second layer comprising a multi-phase oral composition described herein, whereby the bleaching agent is releasably located within the present composition. A suitable first layer may comprise a delivery carrier including a strip of material, a dental tray, a sponge material, and mixtures thereof. In certain embodiments, the delivery carrier may be a strip of material, such as a permanently deformable strip. Suitable strips of material or permanently deformable strips are for example disclosed in U.S. Pat. Nos. 6,136,297; 6,096,328; 5,894,017; 5,891,453; and 5,879,691; and in U.S. Pat. Nos. 5,989,569 and 6,045,811; and in patent application US 2014/0178443 A1.

The delivery carrier may be attached to the teeth via an attachment means that is part of the delivery carrier, for example the delivery carrier may be of sufficient size that, once applied the delivery carrier overlaps with the oral soft tissues rendering more of the teeth surface available for bleaching. The delivery carrier may also be attached to the oral cavity by physical interference or mechanical interlocking between the delivery carrier and the oral surfaces including the teeth.

The delivery carrier may be transparent or translucent to electromagnetic radiation with wavelengths from about 200 nm to about 1700 nm. In certain embodiments, the delivery carrier allows from about 10%, 20%, or 30% to about 40%, 50%, 60%, 70%, 80%, 90%, or 100% of electromagnetic radiation from about 400 nm to about 500 nm to pass through.

Where the delivery carrier is a strip of material, the second layer composition may be coated on the strip, or be applied by the user to the strip, or be applied by the user to the teeth and then the strip may be placed over the coated teeth. The amount of composition applied to the strip or teeth may depend upon the size and capacity of the strip, concentration of the active and the desired benefit; for example from about 0.0001, 0.001 or 0.01 grams to about 0.01, 0.1, 1, or 5 grams may be used or any other numerical range, which is narrower and which falls within such broader numerical range, as if such narrower numerical ranges were all expressly written herein, of composition, in particular from about 0.001 g to about 0.5 g or from about 0.1 g to about 0.4 g of multi-phase oral composition may be used. In addition, from about 0.0001, 0.001 or 0.01 grams to about 0.01, 0.1, 0.5, or 1 grams composition per square centimeter of material ($g/cm^2$) may be used or any other numerical range, which is narrower and which falls within such broader numerical range, as if such narrower numerical ranges were all expressly written herein; in certain embodiments less than about 0.2 $g/cm^2$, from about 0.0001 $g/cm^2$ to about 0.1 $g/cm^2$, or from about 0.01 $g/cm^2$ to about 0.04 $g/cm^2$. In addition, or alternatively, from about 1 microgram to about 5000 micrograms bleaching agent per square centimeter of material (microgram/cm2), preferably from about 10 micrograms/cm2 to about 500 micrograms/cm2, and more preferably from about 50 micrograms/cm2 to about 100 micrograms/cm2 bleaching agent per square centimeter of material may be used.

Figure 2:
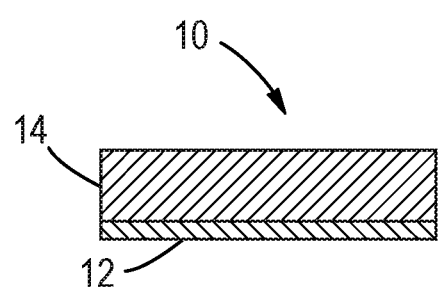
FIG. 2 is a cross-sectional view, taken along section line 2-2 of FIG. 1, showing an example of the strip.

Referring now to the drawings, and more particularly to FIG. 1, there is shown an embodiment of a suitable delivery system 10, representing a delivery system for delivering bleach actives provided by a multi-phase oral composition as disclosed herein to the teeth and the oral cavity. Delivery system 10 comprises a material in strip form 12 of material which is substantially flat, and may have rounded corners. Onto said strip 12 a second layer 14 comprising the present multi-phase oral composition is releasably applied. The second layer 14 may be homogenous and may be uniformly and evenly coated onto strip 12, as shown in the cross-sectional view of FIG. 2. In addition, the second layer 14 comprising the present compositions may be a coating only along a longitudinal axis of a portion of strip of material 12 or may be applied as stripes, spots, and/or other patterns. However, in certain embodiments the second layer 14 may be a laminate or separated layers of components, an amorphous mixture of components, separate stripes or spots or other patterns of different components, or a combination of these structures, including a coating of the second layer 14 along a longitudinal axis of a portion of the strip of material 12.

In certain embodiments, the second layer 14 may contain or is itself an active, such as a composition, compound, or mixture capable of influencing or effecting a desired change in appearance or structure of the surface it contacts. As discussed previously, example actives include: hydrogen peroxide, carbamide peroxide, sodium fluoride, sodium monofluorophosphate, pyrophosphate, chlorhexidine, polyphosphate, triclosan, and enzymes. Examples of appearance and structural changes include, but are not necessarily limited to: whitening, stain bleaching, stain removal, remineralization to form fluorapatite, plaque removal, and tartar removal.

In addition, the second layer 14 composition may comprise adhesive means in order to stably attach the delivery system 10 to the tooth surface. In certain embodiments, the composition as disclosed herein may provide the intended stickiness and adhesiveness by its own, for example by choosing a hydrophobic phase which already provides adhesive properties by adding adhesive material to the compositions of the present invention, or both. In certain embodiments, if added, an adhesive may provide additional properties, such as thickening/rheology modifying properties.

Figure 3:
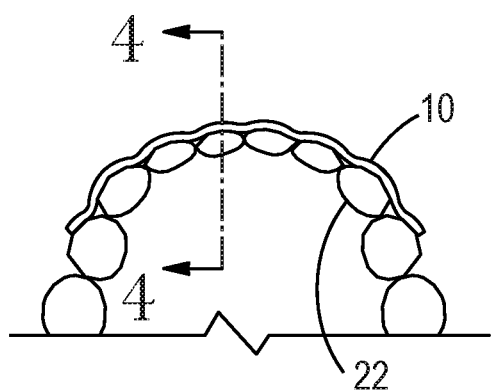
FIG. 3 is a cross-sectional plan view, showing the delivery system 10 attached to the teeth 22 by means of the second layer 14 composition located between the teeth 22 and the strip of material 12.
Figure 4:
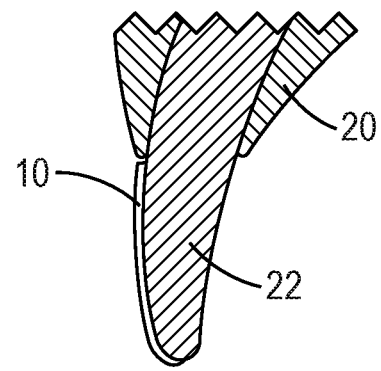
FIG. 4 is a cross-sectional elevation view of a tooth, taken along section line 4-4 of FIG. 3, showing the delivery system 10 adhesively attached to the teeth 22.

FIGS. 3 and 4 show a delivery system 10 of the present invention applied to the tooth surface of a plurality of adjacent teeth. Embedded in adjacent soft tissue 20 is a plurality of adjacent teeth 22. Adjacent soft tissue 20 herein defined as soft tissue surfaces surrounding the tooth structure including: papilla, marginal gingival, gingival sulcus, inter dental gingival, and gingival gum structure on lingual and buccal surfaces up to and including muco-gingival junction on the pallet.

In both FIGS. 3 and 4, delivery system 10 represents a strip 12 and second layer 14 comprising the present composition, wherein the second layer 14 is located on the side of strip of material 12 facing teeth 22. Composition of second layer 14 may be pre-applied to strip of material 12, or may be applied to strip of material 12 by the user prior to application to the teeth. Alternatively, the composition of second layer 14 may be applied directly to teeth 22 by the user and then covered by a strip 12. In any case, strip of material 12 may have a thickness and flexural stiffness such that it can conform to the contoured surfaces of teeth 22 and to adjacent soft tissue 20. Thus, the strip of material 12 may have sufficient flexibility to form to the contours of the oral surface, the surface being a plurality of adjacent teeth 22. The strip 12 may also readily conformable to tooth surfaces and to the interstitial tooth spaces without permanent deformation when the delivery system 10 is applied. The delivery system 10 can be applied without significant pressure.

The first layer 12 of the delivery system 10 may be comprised of a strip of material. Such first layer materials are described in more detail in U.S. Pat. Nos. 6,136,297; 6,096,328; 5,894,017; 5,891,453; and 5,879,691; and in U.S. Pat. Nos. 5,989,569 and 6,045,811; and in patent application US 2014/0178443 A1. The strip 12 serves as a protective barrier for the bleaching agent in the second layer 14. It prevents leaching or erosion of the second layer 14 by for example, the wearer's tongue, lips, and saliva. This allows the active agent in the second layer 14 to act upon the tooth surfaces 22 of the oral cavity for the intended period of time, for example from several minutes to several hours.

The following description of strip of material may apply to the delivery systems 10 with the strip layer 12 as shown in FIGS. 1 to 4 or any form of strips. The strip of material may comprise polymers, natural and synthetic woven materials, non-woven material, foil, paper, rubber and combinations thereof. The strip of material may be a single layer of material or a laminate of more than one layer. Regardless of the number of layers, the strip of material may be substantially water insoluble. The strip material may also be water impermeable. Suitable strip material may be any type of polymer or combination of polymers that meet the required flexural rigidity and are compatible with oral care substances. Suitable polymers include, but are not limited to, polyethylene, ethylvinylacetate, polyesters, ethylvinyl alcohol and combinations thereof. Examples of polyesters include Mylar® and fluoroplastics such as Teflon®, both manufactured by Dupont. In certain embodiments, the material used as strip of material is polyethylene. The strip of material may be less than about 1 mm (millimeter) thick, less than about 0.05 mm thick, or from about 0.001 to about 0.03 mm thick. A polyethylene strip of material may be less than about 0.1 mm thick or from about 0.005 to about 0.02 mm thick.

In certain embodiments, the present invention may comprise a dissolvable film, which can be adhered to the oral cavity thereby releasing an active, the dissolvable film comprising water-soluble polymers, one or more polyalcohols, and one or more actives. In addition to one or more actives, a dissolvable film may contain a combination of certain plasticizers or surfactants, colorants, sweetening agents, flavors, flavor enhancers, or other excipients commonly used to modify the taste of formulations intended for application to the oral cavity. The resulting dissolvable film is characterized by an instant wettability which causes the dissolvable film to soften soon after application to the mucosal tissue, thus preventing the user from experiencing any prolonged adverse feeling in the mouth, and a tensile strength suitable for normal coating, cutting, slitting, and packaging operations.

The dissolvable film may comprise a water-soluble polymer or a combination of water-soluble polymers, one or more plasticizers or surfactants, one or more polyalcohols, and an active.

The polymers used for the dissolvable film include polymers which are hydrophilic and/or water-dispersible. Examples of polymers that can be used include polymers that are water-soluble cellulose-derivatives, such as hydroxypropylmethyl cellulose, hydroxyethyl cellulose, or hydroxypropyl cellulose, either alone, or mixtures thereof. Other optional polymers, without limiting the invention, include polyvinyl pyrrolidone, carboxymethyl cellulose, polyvinyl alcohol, sodium alginate, polyethylene glycol, natural gums like xanthane gum, *tragacantha*, guar gum, acacia gum, arabic gum, water-dispersible polyacrylates like polyacrylic acid, methylmethacrylate copolymer, carboxyvinyl copolymers. The concentration of the water-soluble polymer in the final film can very between 20 and 75% (w/w), or between 50 and 75% (w/w).

The surfactants that may be used for the dissolvable film may be one or more nonionic surfactants. When a combination of surfactants is used, the first component may be a polyoxyethylene sorbitan fatty acid ester or a ALPHA-hydro-OMEGA-hydroxypoly (oxyethylene)poly(oxypropylene)poly(oxyethylene) block copolymer, while the second component may be a polyoxyethylene alkyl ether or a polyoxyethylene castor oil derivative. In certain embodiments, the HLB value of the polyoxyethylene sorbitan fatty acid ester should be between 10 and 20, whereby a range of 13 to 17 may also be used. The ALPHA-hydro-OMEGA-hydroxypoly(oxyethylene)poly(oxypropylene) poly(oxyethylene) block copolymer may contain at least about 35 oxypropylene-units, and in certain embodiments not less than about 50 oxypropylene-units.

The polyoxyethylene alkyl ether may an HLB value between 10 and 20, and in certain embodiments an HLB value of not less than 15 may be used. The polyoxyethylene castor oil derivative may have an HLB value of 14-16.

In order to achieve the desired instant wettability, the ratio between the first and second component of the binary surfactant mixture may be kept within 1:10 and 1:1, or between 1:5 and 1:3.

The total concentration of surfactants in the dissolvable film depends on the properties of the other ingredients, but usually may be between 0.1 and 5% (w/w).

The polyalcohol can be used to achieve a desired level of softness of the dissolvable film. Examples of polyalcohols include glycerol, polyethylene glycol, propylene glycol, glycerol monoesters with fatty acids or other pharmaceutically used polyalcohols. The concentration of the polyalcohol in the dry film usually ranges between 0.1 and 5% (w/w).

The shape of the strip of material may be any shape or size that covers the desired oral surface. For example, in certain embodiments the strip of material may have rounded corners to avoid irritation of the soft tissue of the oral cavity. "Rounded corners," as used herein means generally lacking sharp angles or points, for example one or more angles of 135° or less. The length of the strip of material may be from about 2 cm (centimeter) to about 12 cm, or from about 4 cm to about 9 cm. The width of the strip of material may also depend on the oral surface area to be covered. The width of the strip of material may be from about 0.5 cm to about 4 cm or from about 1 cm to about 2 cm. The strip or material may be worn as a patch on one or several teeth to treat a localized condition.

The strip of material may contain shallow pockets. When the multi-phase oral composition is coated on a strip of material, bleach agents and/or oral care actives, fill shallow pockets to provide reservoirs of additional bleach agents and/or oral care actives. Additionally, the shallow pockets help to provide texture to the delivery system. The strip of material may have an array of shallow pockets. Generally, the shallow pockets are approximately 0.4 mm across and about 0.1 mm deep. When shallow pockets are included in the strip of material and multi-phase oral compositions herein are applied to it in various thicknesses, in certain embodiments the overall thickness of the delivery system is less than about 1 mm, in certain embodiments the overall thickness is less than about 0.5 mm.

Flexural stiffness is a material property that is a function of a combination of strip of material thickness, width and material modulus of elasticity. The test described below is a method for measuring the rigidity of films, such as polyolefin film and sheeting. It determines the resistance to flexure of a sample by using a strain gauge affixed to the end of a horizontal beam. The opposite end of the beam presses across a strip of the sample to force a portion of the strip into a vertical groove in a horizontal platform upon which the sample rests. A microammeter wired to the strain gauge is calibrated in terms of deflection force. The rigidity of the sample is read directly from the microammeter and expressed as grams per centimeter of the sample strip width. In certain embodiments, a strip of material which is suitable to be used as delivery carrier of the compositions as disclosed herein may show a flexural stiffness of less than about 5 grams/cm as measured on a Handle-O-Meter, model #211-300, available from Thawing-Albert Instrument Company of Philadelphia, Pa. as per test method ASTM D2923-95. The strip may have a flexural stiffness less than about 3 grams/cm, less than about 2 grams/cm or a flexural stiffness from about 0.1 to about 1 grams/cm. Generally, the flexural stiffness of the strip of material may be substantially constant and does not change during normal use. For example, the strip of material does not need to be hydrated for the strip to achieve the low flexural stiffness in the above-specified ranges. This relatively low stiffness enables the strip of material to cover the contours of the oral surface with very little force being exerted. That is, conformity to the contours of the oral surface of the wearer's mouth is maintained because there is little residual force within the strip of material to cause it to return to its shape just prior to its application to the oral surface, i.e. substantially flat. For example, in certain embodiments a strip of material's flexibility enables it to contact soft tissue over an extended period of time without irritation; such that a strip of material does not require pressure for retention against the oral surface.

The delivery systems as used herein may comprise an adhesion means, such that they are capable of adhesion to oral surfaces, especially the teeth. This adhesion means may be provided by the present compositions herein or the adhesion means may be provided independently of the compositions herein (for example the adhesion means is a separate phase from the compositions herein where the compositions may also have an adhesive means). In certain embodiments, the strip of material may be held in place on the oral surface by adhesive attachment provided by the present composition. The viscosity and general tackiness of the multi-phase oral composition to dry surfaces may cause the strip to be adhesively attached to the oral surface without substantial slippage from the frictional forces created by the lips, teeth, tongue, and other oral surfaces rubbing against the strip of material while talking drinking, etc. However, this adhesion to the oral surface may be low enough to allow the strip of material to be easily removed by the wearer by simply peeling off the strip of material using one's finger. The delivery system may be easily removable from the oral surfaces without the use of an instrument, a chemical solvent or agent or excess friction.

In addition, in certain embodiments the strip of material may be held in place on the oral surface by adhesive means and attachment provided by the delivery carrier itself. For example, the strip of material can extend, attach, and adhere to the oral soft tissue. In addition, in certain embodiments an adhesive can be applied to that portion of the strip of material that will attach the delivery systems to the oral soft tissue. The delivery carrier may also be attached to the oral cavity by physical interference or mechanical inter-locking between the delivery carrier and the oral surfaces including the teeth. In addition, the strip of material may be held in place by an adhesion means that is independent of the composition of the present inventions herein, as disclosed in WO 03/015656.

Suitable adhesion means are known to the skilled person. When the adhesive means, if present, is provided by an adhesive, the adhesive may be any adhesive which may be used to adhere materials to the tooth surface or to a surface of the oral cavity surfaces. Suitable adhesives include, but are not limited to, skin, gum and muco adhesives, and should be able to withstand the moisture, chemicals and enzymes of the oral environment for long enough for the oral care actives and/or bleach to take effect, but may be soluble and/or biodegradable thereafter. Suitable adhesives may for example comprise water soluble polymers, hydrophobic and/or non-water soluble polymers, pressure and moisture sensitive adhesives, e.g. dry adhesives which become tacky upon contact with the mouth environment, e.g. under the influence of moisture, chemicals or enzymes etc. in the mouth. Suitable adhesives include natural gums, synthetic resins, natural or synthetic rubbers, those gums and polymers listed above under "Thickening Agents", and various other tacky substances of the kind used in known adhesive tapes, those known from U.S. Pat. No. 2,835,628.

The delivery carrier, such as a strip, as shown for example in FIGS. 1 to 4, may be formed by several of the film making processes known in the art. For example, a strip of polyethylene is made by a blown process or a cast process. Other processes including extrusion or processes that do not affect the flexural rigidity of the strip of material are also feasible. In addition, the present compositions forming a second layer onto the strip may be incorporated onto the strip during the processing of the strip and/or the present composition may be a laminate layer on the strip. The second layer attached to the strip of such a delivery system as disclosed above comprises a safe and effective amount of the present composition described herein.

In addition, the delivery system may comprise an optional release liner. Such a release liner may be formed from any material which exhibits less affinity for the second layer composition than the second layer composition exhibits for itself and for the first layer strip of material. The release liner may comprise a rigid sheet of material such as polyethylene, paper, polyester, or other material, which is then coated with a nonstick type material. The release liner may be cut to substantially the same size and shape as the strip of material or the release liner may be cut larger than the strip of material to provide a readily accessible means for separating the material from the strip. The release liner may be formed from a brittle material that cracks when the strip is flexed or from multiple pieces of material or a scored piece of material. Alternatively, the release liner may be in two overlapping pieces such as a typical adhesive bandage design. A description of materials suitable as release agents is found in Kirk-Othmer, Encyclopedia of Chemical Technology, Fourth Edition, Volume 21, pp. 207-218, incorporated herein by reference.

In certain embodiments, the delivery carrier may be a permanently deformable strip of material having a yield point and thickness such that the strip of material substantially conforms to a shape of a tooth via permanent deformation under a pressure less than about 250,000 Pascals as it has been found that wearers will press a strip onto each tooth using one fingertip having about one square centimeter surface area. They typically apply force at each tooth for one second or less with a typical application pressure ranging from about 100,000 Pascals to about 250,000 Pascals.

In certain embodiments, a strip of material has viscoelastic properties which enable it to creep as well as bend in order to conform across several teeth and around the arch of the wearer's mouth. It is important that the necessary permanent deformation occurs under minimum normal force being applied by the wearer.

The multi-phase oral composition may also be applied to the tooth surface and may be covered with the deformable strip before or after it has been shaped. In addition or alternatively, the multi-phase oral composition may be applied to the deformable strip as pre-coating and may be applied together with the strip to the tooth surface before or after the deformable strip has been shaped, wherein the strip is applied such that when the delivery system is placed on a surface of the tooth, the multi-phase oral composition contacts the tooth surface providing an active onto the tooth surface. In addition or alternatively, the deformable strip of material may be applied to the teeth with a force sufficient to shape the delivery carrier such that it at least partially conforms to the shape of the teeth, then the shaped strip of material may be removed from the tooth surface, the oral care composition may be applied to the shaped strip of material, and the shaped strip of material may be re-applied to the tooth surface such that it at least partially conforms to a shape of the tooth and contacts the oral care composition against the tooth surface. If the deformable strip is applied together with the multi-phase oral composition to the tooth surface the multi-phase oral composition may also comprise adhesive agents to hold the delivery system in place for a sufficient time to allow the active of the multi-phase oral composition to act upon the surface. The multi-phase oral composition, if used together with a deformable strip, may have an extrusion resistance sufficient to withstand a normal force applied to shape the deformable strip of material so that the substance is not substantially extruded from between the deformable strip of material and the surface during manual shaping of the deformable strip of material. By "substantially extruded from" is meant that at least 50% or more of the multi-phase oral composition is extruded from between the deformable strip of material and the tooth and adjoining soft tissue surfaces.

The deformable strip of material may be made of a permanently deformable material, such as wax, putty, tin or foil, as a single layer or a combination of layers or materials, such as a laminate. In certain embodiments, the deformable strip may be wax, such as #165 sheet wax formulated and manufactured by Freeman Mfg. & Supply Co. of Cleveland, Ohio. This particular wax readily conforms to the shape of a tooth under a pressure of about 133,000 Pascal which is the pressure generated when the wearer applies a normal force of about 3 pounds (1.36 kg) over an area of about one square centimeter. The deformable strip of material may have a nominal film thickness of about 0.8 mm, wherein the deformable strip may be substantially flat and rectangular in shape with rounded corners. The deformable strip of material may have a length sufficient to cover a plurality of adjacent teeth while conforming to the curvature of the wearer's mouth and gaps between the adjacent teeth. If the deformable strip of material includes the multi-phase oral composition coated thereon, the multi-phase oral composition may have an overall thickness less than about 1.5 mm. Deformable strips as disclosed herein may also be used as the material for the strip of material 12 shown in FIGS. 1 to 4. Thus, general features of a strip of material as described above for example with respect to FIGS. 1 to 4 may also apply to the deformable strip of material. In addition, a release liner and/or shallow pockets may also be combined with a deformable strip of material.

Figure 5:
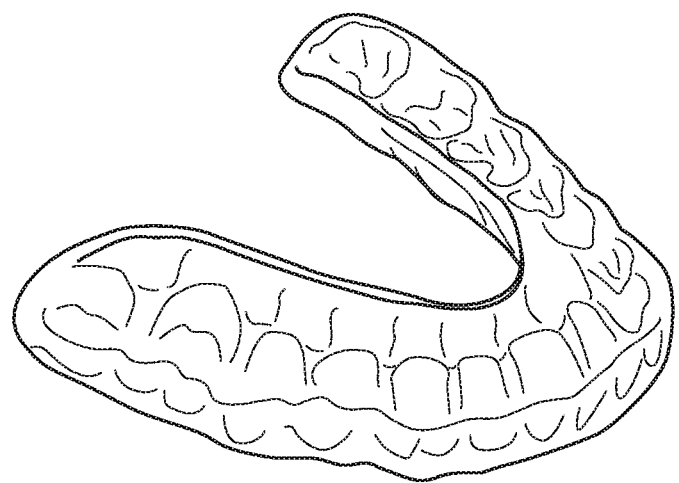
FIG. 5 shows a dental tray 30 suitable to be used with the composition of the present invention.

The present compositions may be used in combination with a delivery carrier including a dental tray and/or foam material. Dental trays are well known in the whitening art and an example dental tray 30 is shown in FIG. 5. The general process for preparing dental trays 30 is known in the art. Dentists have traditionally utilized three types of dental appliances for bleaching teeth.

The first type is a rigid appliance which is fitted precisely to the patient's dental arches. For example, an alginate impression which registers all teeth surfaces plus gingival margin is made and a cast is promptly made of the impression. If reservoirs are desired they are prepared by building a layer of rigid material on the cast on specific teeth surfaces to be treated. A dental tray is then vacuum formed from the modified cast using conventional techniques. Once formed, the tray is preferably trimmed barely shy of the gingival margin on both buccal and lingual surfaces. Enough tray material should be left to assure that all of the tooth will be covered to within about ¼ to about ⅓ mm of the gingival border upon finishing and beveling the tray periphery. One can scallop up and around interdental papilla so that the finished tray does not cover them. All tray edges are preferably smoothed so that the lip and tongue will not feel an edge prominence. The resulting tray, provides a perfect fit of the patient's teeth optionally with reservoirs or spaces located where the rigid material was placed on the cast. Dental trays may comprise of soft transparent vinyl material having a thickness from about 0.1 cm to about 0.15 cm. Soft material is more comfortable for the patient to wear. Harder material (or thicker plastic) may also be used to construct the tray.

A second type of rigid custom dental appliance is an "oversized" rigid custom dental appliance. The fabrication of rigid, custom dental appliances entails fabricating cast models of the patient's dental arch impressions, and heating and vacuum-forming a thermoplastic sheet to correspond to the cast models of a patient's dental arches. Thermoplastic films are sold in rigid or semi rigid sheets and are available in various sizes and thickness. The dental laboratory fabrication technique for the oversized rigid dental appliance involves augmenting the facial surfaces of the teeth on the cast models with materials such as die spacer or light cured acrylics. Next, thermoplastic sheeting is heated and subsequently vacuum formed around the augmented cast models of the dental arch. The net effect of this method results in an "oversized" rigid custom dental appliance.

A third type of rigid custom dental appliance, used with less frequency, is a rigid bilaminated custom dental appliance fabricated from laminations of materials, ranging from soft porous foams to rigid, non-porous films. The non-porous, rigid thermoplastic shells of these bilaminated dental appliances encase and support an internal layer of soft porous foam.

A fourth type of dental tray replaces rigid custom dental appliances with disposable U-shaped soft foam trays, which may be individually packaged, and which may be saturated with a pre-measured quantity of the composition of the present invention. The soft foam material is generally an open celled plastic material. Such a device is commercially available from Cadco Dental Products in Oxnard, Calif. under the tradename VitalWhite™. These soft foam trays may comprise a backing material (e.g. a closed cell plastic backing material) to minimize the elution of the bleaching agent from the device, into the oral cavity to minimize ingestion by the patient and/or irritation of the oral cavity tissues. Alternatively, the soft foam tray is encased by a nonporous flexible polymer or the open cell foam is attached to the frontal inner wall of the dental appliance and/or the open cell foam is attached to the rear inner wall of the dental appliance. Those of ordinary skill in the art will readily recognize and appreciate, that the present compositions must be thick enough not to simply run out between the open cell structure of the foam and must be thin enough to slowly pass through the open cell foam over time. In other words, the open cell foam material has an internal structural spacing sized relative to the viscosity of the compositions to absorb and allow the composition to pass there through.

An example of a closed cell material is a closed-cell polyolefin foam sold by the Voltek division of Sekisui America Corporation of Lawrence, Mass. under the tradename Volora which is from 1/32" to 1/8" in thickness. A closed cell material may also comprise of a flexible polymeric material. An example of an opened cell material is an open celled polyethylene foam sold by the Sentinel Foam Products division of Packaging Industries Group, Inc. of Hyannis, Mass. under the tradename Opcell which is from 1/16" to 3/8" in thickness. Other open cell foam useful herein include hydrophilic open foam materials such as hydrogel polymers (e.g Medicell™ foam available from Hydromer, Inc. Branchburg, J.J.). Open cell foam may also be hydrophilic open foam material imbibed with agents to impart high absorption of fluids, such as polyurethane or polyvinylpyrrolidone chemically imbibed with various agents.

Preparation of the Present Multi-Phase Oral Compositions

Principally, preparation of particles-in-semisolid dispersions is well known in the art and any suitable manufacturing process can be used to make the multi-phase oral compositions which may be in the form of an particles-in-semisolid dispersion. Generally, the components are separated into those that are hydrophilic and those that are hydrophobic. The two phases are then mixed, with heating if necessary, and the product is stirred and then optionally cooled. After combining the phases, the present multi-phase oral compositions, which may be in the form of particles-in-semisolid dispersions may be agitated or sheared by various methods, including shaking, intermittent shaking, high shear mixing, or by using high speed mixers, blenders, colloid mills, homogenizers, or ultrasonic techniques.

In certain embodiments, multi-phase oral compositions, which may be in the form of an particles-in-semisolid dispersion, as disclosed herein may be made as follows: prepare the hydrophilic bleaching agent particles and hydrophobic phase; combine the hydrophilic bleaching agent particles and the hydrophobic phase in a mixing vessel and mix well with any means known within the art, for example, a Speedmixer (from Flacktek Inc., Landrum, S.C.) may be used to make multi-phase oral compositions, which may be in the form of an particles-in-semisolid dispersion, of the present invention. The mixing procedure of the SpeedMixer™ series is based on the double rotation of the mixing cup using a dual asymmetric centrifugal mixing. This combination of centrifugal forces acting on different levels enables very rapid mixing of the entire cup. Optionally the composition may be heated, if necessary to facilitate mixing. Continue mixing the composition until uniform. When the active is included in solid particulate form, the addition of an optional viscosity modifier, such as silica, may be appropriate to keep the particulate dispersed and suspended within the composition. Flavorants or sweeteners may also be added to one of the phases of the composition, as desired. Thereafter the composition may be added to the delivery carrier, as desired.

MULTI-PHASE ORAL COMPOSITION
PROPHETIC FORMULATION EXAMPLES

The following non-limiting Prophetic Formulation examples further describe embodiments expected to be within the scope of the present invention. Many variations of these examples are possible without departing from the scope of the invention.

Prophetic Formulation Examples I

Prophetic Formulation Examples I may be made using any suitable procedure disclosed above and formulated with urea peroxide. These examples illustrate compositions that may be made with 1) the concentration of urea peroxide in the overall composition ranging from 0.0277% to 33.1872%, 2) the concentration of $H_2O_2$ (incorporated in the urea peroxide) in the overall composition ranging from 0.01% to 12%, and 3) the ratio of the concentration in weight percent of $H_2O_2$ present in the hydrophilic bleaching agent particles to the concentration in weight percent of $H_2O_2$ present in the overall composition ranging from 3.01 to 3615.85.

| Prophetic Formulation Examples I | A (Wt %) | B (Wt %) | C (Wt %) | D (Wt %) | E (Wt %) | F (Wt %) | G (Wt %) |
|---|---|---|---|---|---|---|---|
| Urea Peroxide[1] | 33.187 | 16.594 | 8.297 | 5.531 | 2.766 | 0.277 | 0.028 |
| Petrolatum[2] | 66.813 | 83.406 | 91.703 | 94.469 | 97.234 | 99.723 | 99.972 |
| total | 100.00 | 100.00 | 100.00 | 100.00 | 100.00 | 100.00 | 100.00 |
| % $H_2O_2$ in total oral composition (calculated) | 12.000 | 6.000 | 3.000 | 2.000 | 1.000 | 0.100 | 0.010 |
| % $H_2O_2$ in Peroxide (theoretical calculated molecular formula) | 36.16 | 36.16 | 36.16 | 36.16 | 36.16 | 36.16 | 36.16 |
| RATIO* | 3.01 | 6.03 | 12.05 | 18.08 | 36.16 | 361.59 | 3615.85 |

Prophetic Formulation Examples II

Prophetic Formulation Examples II may be made using any suitable procedure disclosed above and formulated with urea peroxide. These examples illustrate compositions that may be made with 1) the concentration of a complex of hydrogen peroxide and polyvinylpyrrolidone (PVP) polymer in the overall composition ranging from 0.0541% to 64.8649%, 2) the concentration of $H_2O_2$ (incorporated in the complex of hydrogen peroxide and polyvinylpyrrolidone (PVP) polymer) in the overall composition ranging from 0.01% to 12%, and 3) the ratio of the concentration in weight percent of $H_2O_2$ present in the hydrophilic bleaching agent particles to the concentration in weight percent of $H_2O_2$ present in the overall composition ranging from 1.54 to 1850.

surfaces of the oral cavity are neither required to be clean, nor to be dried nor to be excessively wet with saliva or water before the application. However, it is believed that adhesion to the tooth enamel surfaces will be improved if the teeth are dry prior to application.

Dental tray appliances may be used as follows. The patient or dental professional dispenses the present composition into a soft or rigid dental appliance and then the participant places the appliance over the participant's dental arch (or fits the device around his or her teeth to keep the tray in position). Generally, the recommended treatment period is a sufficient period of time to achieve whitening as disclosed above. At the end of the treatment period, the dental appliance is removed, cleaned with water to remove any remaining composition, and then stored until the next application.

| Prophetic Formulation Examples II | A (Wt %) | B (Wt %) | C (Wt %) | D (Wt %) | E (Wt %) | F (Wt %) | G (Wt %) |
|---|---|---|---|---|---|---|---|
| Complex of hydrogen peroxide and PVP[1] | 64.865 | 32.432 | 16.216 | 10.811 | 5.405 | 0.541 | 0.0541 |
| Petrolatum[2] | 35.135 | 67.568 | 83.784 | 89.189 | 94.595 | 99.459 | 99.9459 |
| total | 100.00 | 100.00 | 100.00 | 100.00 | 100.00 | 100.00 | 100.00 |
| % $H_2O_2$ in total composition (calculated) | 12.00 | 6.00 | 3.00 | 2.00 | 1.00 | 0.10 | 0.01 |
| % $H_2O_2$ in Complex of hydrogen peroxide and PVP[3] | 18.50 | 18.50 | 18.50 | 18.50 | 18.50 | 18.50 | 18.50 |
| RATIO* | 1.54 | 3.08 | 6.17 | 9.25 | 18.50 | 185.00 | 1850.00 |

*RATIO of the concentration in weight percent of $H_2O_2$ present in the hydrophilic bleaching agent particles to the concentration in weight percent of $H_2O_2$ present in the overall composition
[1]Peroxydone K-30, from Ashland Global Specialty Chemicals Inc., Covington, KY. Sieved through USA Standard Testing Sieve Number 40 with 425 micron opening.
[2]G-2218 Grade from Sonneborn, LLC., Parsippany, NJ
[3]mid-value of range provided by supplier brochure Methods of Using the Compositions and/or Delivery Systems The present invention can be applied to the teeth of a consumer in the dental office by a dental professional, or can be used at home by the consumer. Generally, the recommended treatment period is a sufficient period of time to achieve whitening.

In practicing the present invention, the user applies the composition herein that contains the bleaching agent to obtain the desired effect, such as, whitening, to one or more teeth. The composition can be applied with a paint-on device, a syringe or unit dose syringe, squeezable tube, a brush, a pen or brush tip applicator, a doe's foot applicator, swab, lip gloss applicator, strip that is removed after application, tray that is removed after application, or the like, or even with the fingers. The composition can also be combined with a delivery carrier, such as a strip of material, a dental tray, or a sponge material, and thereafter applied to the teeth. In certain embodiments, the compositions or delivery systems herein are almost unnoticeable when applied to the teeth. After a desired period of time has elapsed, any residual composition may be easily removed by wiping, brushing or rinsing the oral surface.

In general, it is not necessary to prepare the teeth before applying the present composition. For example, the user may choose to brush the teeth or rinse the mouth before applying the compositions of the present invention, but the The above-described compositions and delivery systems may be combined in a kit which comprises: 1. present composition and 2. instructions for use; or which comprises: 1. present composition, 2. instructions for use, and 3. a delivery carrier. In addition, if the tooth shall be radiated by electromagnetic radiation, the kit may further comprise an electromagnetic radiation source of the appropriate wavelength and instruction for use, so that the kit can be used by consumers in a convenient manner.

Optional Electromagnetic Radiation Treatment

The multi-phase oral composition as disclosed herein may be used to whiten teeth and/or removing stain from tooth surfaces. In addition, the bleaching efficacy may be further increased by directing electromagnetic radiation of a suitable wavelength toward at least one tooth. A device suitable to provide such electromagnetic radiation is shown in FIG. 6. A suitable wavelength may be any wavelength, which corresponds to a maximum absorption band of the tooth and/or the tooth stain to be bleached. For example, the multi-phase oral composition may be radiated with an electromagnetic radiation with one or more wavelengths in the range of from about 200 nm to about 1200 nm. The electromagnetic radiation may be directed toward at least one tooth. In addition, more than one tooth may be irradiated. In particular, the electromagnetic radiation may have a peak intensity at a wavelength in the range of from about 400, 405, 410, 415, 420, 425, 430, 435, 440, or 445, 446 nm to about 450, 455, 460, 465, 470, 475, 480, 481, 485, 490, 495, or 500 nm or any other numerical range, which is narrower and which falls within such broader numerical range, as if such narrower numerical ranges were all expressly written herein. In certain embodiments, the electromagnetic radiation has a peak intensity at a wavelength in the range of from about 425 nm to about 475 nm, from about 445 nm to about 465 nm, or wherein the peak intensity wavelength of the electromagnetic radiation is similar to the wavelength at which the stain absorbs the most electromagnetic radiation. Electromagnetic radiation may be directed toward at least one tooth for partial or whole wearing time of the composition; or after the composition has been removed from the tooth. Electromagnetic radiation may be applied at least for a sufficient period of time for whitening, e.g. for at least about 1 minute, for at least about 5 minutes, or for at least about 10 min. The electromagnetic radiation may be applied using the procedure disclosed in US 2013/0295525. Preferably the multi-phase oral composition as disclosed herein is applied to at least one tooth and maintained on the at least one tooth for a first period of time; after the first period of time electromagnetic radiation is directed toward the at least one tooth for a second period of time, wherein the first period of time has a duration greater than 50%, preferably 80% of a total duration of the first and second periods of time; and finally, the multi-phase oral composition is removed from the at least one tooth.

Suitable sources of electromagnetic radiation include the source described herein in the section titled "Clinical Protocol".

The multi-phase oral compositions as disclosed herein may be transparent or translucent to electromagnetic radiation with wavelengths from about 400 nm to about 500 nm. In certain embodiments, the multi-phase oral compositions as disclosed herein when applied in a thickness of from about 0.0001, 0.001, or 0.01 cm to about 0.01, 0.1, or 0.5 cm thick allow from about 10%, 20%, or 30% to about 40%, 50%, 60%, 70%, 80%, 90%, or 100% of electromagnetic radiation from about 400 nm to about 500 nm to pass through, as measured by a spectrophotometer. In certain embodiments, when a multi-phase oral composition is applied in a thickness of about 0.1 cm, from about 80% to about 100% of electromagnetic radiation from about 400 nm to about 500 nm passes through, as measured by a spectrophotometer. The multi-phase oral compositions, as disclosed herein, may when applied in an amount from about 0.0001, 0.001, or 0.01 grams to about 0.01, 0.1, 1, or 5 grams, on a delivery carrier or tray with a surface area from about 5 $cm^2$ to about 20 $cm^2$, allow from about 10%, 20%, or 30% to about 40%, 50%, 60%, 70%, 80%, 90%, or 100% of electromagnetic radiation from about 400 nm to about 500 nm to pass through.

The electromagnetic radiation impinging on the surface of the tooth or outer surface of the carrier, which may be a strip, in the wavelength range from about 400 to about 500 nm may range in intensity from about 5, 10, 25, 50, 75, or 100 mW/cm2 to about 500, 250, 225, 205, 200, 175, 150, 125, 100, 75, 50, 25, 10, or 5 mW/cm2 or any other numerical range, which is narrower and which falls within such broader numerical range, as if such narrower numerical ranges were all expressly written herein.

Procedure to Measure Intensity of Electromagnetic Radiation

The intensity of the electromagnetic radiation can be measured using a spectrometer (USB 2000+ from Ocean Optics) connected to a UV-VIS 200 micron fiber-optic cable with a cosine corrector at the tip (OP 200-2-UV-VIS from Ocean Optics). The spectrometer is connected to a computer running the spectrometer software (Oceanview 1.3.4 from Ocean Optics). The tip of the fiber-optic cable is held pointing toward the light source at the location where the light intensity is to be measured. The photons collected at the detector surface are guided via the fiber-optic cable to the charge-coupled device in the spectrometer (CCD). The CCD counts photons arriving to the CCD during a pre-determined time period at each wavelength from 200 nm to 1100 nm, and uses a software algorithm to convert these photon counts to spectral irradiance (mW/$cm^2$/nm). The spectral irradiance is integrated from 200 nm to 1100 nm by the software to yield the Absolute Irradiance (mW/$cm^2$), which is the intensity of electromagnetic radiation from 200 nm to 1100 nm. The spectral irradiance is integrated from 400 nm to 500 nm by the software to yield the Absolute Irradiance (mW/$cm^2$), which is the intensity of electromagnetic radiation from 400 nm to 500 nm.

For consumer convenience, the multi-phase oral composition as disclosed herein may be provided as a Kit comprising the bleaching composition as disclosed herein, a delivery carrier for easier application, an electromagnetic radiation source emitting electromagnetic radiation in a suitable wavelength, and instructions for use.

The compositions of this invention are useful for both human and other animals (e.g. pets, zoo, or domestic animals) applications.

EXAMPLES

The following non-limiting examples further describe preferred embodiments within the scope of the present invention. Many variations of these examples are possible without departing from the scope of the invention. All examples were performed at room temperature (RT) and atmospheric pressure unless stated otherwise. These multi-phase oral compositions were made as described previously or below.

Preparation of Multi-Phase Compositions

A 500-gram batch of Example I and II was made by weighing the Urea Peroxide (Ex. 1) or the complex of hydrogen peroxide and polyvinylpyrrolidone polymer (Ex. 2) (hydrophilic bleaching agent particles) and petrolatum into a Speedmixer container ("Max 300 Long Cup Translucent", item number 501 218t from Flacktek Inc., Landrum, S.C.), and mixing in a Speedmixer at 800 RPM for 5 seconds, 1200 RPM for 5 seconds, and 1950 RPM for 2 minutes. The walls of the container were then scraped down with a plastic spatula, and the contents were mixed a second time at 800 RPM for 5 seconds, 1200 RPM for 5 seconds, and 1950 RPM for 2 minutes. The walls of the container were then scraped down with a plastic spatula, and the contents were mixed a third time at 800 RPM for 5 seconds, 1200 RPM for 5 seconds, and 1950 RPM for 2 minutes.

A 50-gram batch of Example II was made by weighing the complex of hydrogen peroxide and polyvinylpyrrolidone polymer (hydrophilic bleaching agent particles) and petrolatum into a Speedmixer container ("Max 100 Long Cup Translucent", item number 501 221Lt from Flacktek Inc., Landrum, S.C.), and mixing in a Speedmixer at 800 RPM for 5 seconds, 1200 RPM for 5 seconds, and 1950 RPM for 2 minutes. The walls of the container were then scraped down with a plastic spatula, and the contents were mixed a second time at 800 RPM for 5 seconds, 1200 RPM for 5 seconds, and 1950 RPM for 2 minutes. The walls of the container were then scraped down with a plastic spatula, and the contents were mixed a third time at 800 RPM for 5 seconds, 1200 RPM for 5 seconds, and 1950 RPM for 2 minutes.

A 50-gram batch of Example III was made by weighing the complex of hydrogen peroxide and polyvinylpyrrolidone polymer (hydrophilic bleaching agent particles), sodium bicarbonate, mineral oil, and petrolatum into a Speedmixer container ("Max 100 Long Cup Translucent", item number 501 221Lt from Flacktek Inc., Landrum, S.C.), and mixing in a Speedmixer at 800 RPM for 5 seconds, 1200 RPM for 5 seconds, and 1950 RPM for 2 minutes. The walls of the container were then scraped down with a plastic spatula, and the contents were mixed a second time at 800 RPM for 5 seconds, 1200 RPM for 5 seconds, and 1950 RPM for 2 minutes. The walls of the container were then scraped down with a plastic spatula, and the contents were mixed a third time at 800 RPM for 5 seconds, 1200 RPM for 5 seconds, and 1950 RPM for 2 minutes.

A summary of Ex. I-III is provided in TABLE 1.

TABLE 1

| Example I-III | Ex. 1 | Ex. II | Ex. III |
|---|---|---|---|
| Urea Peroxide[1] | 8.4746 | — | — |
| Complex of hydrogen peroxide and polyvinylpyrrolidone polymer[2] | — | 16.2162 | 16.2162 |
| Petrolatum[3] | 91.5254 | 83.7838 | 15.1352 |
| Sodium Bicarbonate[4] | — | — | 48.6486 |
| Mineral Oil[5] | — | — | 20.0000 |
| total | 100.00 | 100.0 | 100.0 |
| % $H_2O_2$ | 3.0 | 3.0 | 3.0 |
| Solubility of Urea Peroxide (Ex. I) or Complex of hydrogen peroxide and polyvinylpyrrolidone polymer (Ex. II and Ex. III) in Water (number of parts by weight per 100 parts by weight of water) | 80 | >40 | >40 |

[1]Urea Hydrogen Peroxide Adduct, Catalog number L13940 from Alfa Aesar, Ward Hill, MA Solubility in water of 800 grams per liter at 20 C. per Safety Data Sheet from supplier (80 parts per 100 parts of water). Sieved through USA Standard Testing Sieve Number 40 with 425 micron opening.
[2]Peroxydone K-30, from Ashland Global Specialty Chemicals Inc., Covington, KY. Solubility >40 parts per 100 parts of water (estimated from information provided in Product Data Sheet from supplier on polyvinylpyrrolidone polymer K-30). Sieved through USA Standard Testing Sieve Number 40 with 425 micron opening.
[3]G-2218 Grade from Sonneborn, LLC., Parsippany, NJ
[4]USP No. 2 grade from Genesis Specialty Alkali LLC, Philadelphia, PA
[5]Kaydol White Mineral Oil Grade from Sonneborn, LLC., Parsippany, NJ Comparative Example I A 500-gram batch of Comparative Example-I was made by weighing the Sodium percarbonate (hydrophilic bleaching agent particles) and petrolatum into a Speedmixer container ("Max 300 Long Cup Translucent", item number 501 218t from Flacktek Inc., Landrum, S.C.), and mixing in a Speedmixer at 800 RPM for 5 seconds, 1200 RPM for 5 seconds, and 1950 RPM for 2 minutes. The walls of the container were then scraped down with a plastic spatula, and the contents were mixed a second time at 800 RPM for 5 seconds, 1200 RPM for 5 seconds, and 1950 RPM for 2 minutes. The walls of the container were then scraped down with a plastic spatula, and the contents were mixed a third time at 800 RPM for 5 seconds, 1200 RPM for 5 seconds, and 1950 RPM for 2 minutes. A summary of Comp. Ex. I is provided in TABLE 2.

TABLE 2

| Comparative Example I | (Wt %) |
|---|---|
| Sodium Percarbonate[1] | 9.2320 |
| Petrolatum[2] | 90.7680 |
| total | 100.00 |
| % $H_2O_2$ in total oral composition (calculated) | 3.0 |
| % $H_2O_2$ in Sodium Percarbonate (theoretical value calculated from molecular formula) | 32.50 |
| RATIO* | 10.84 |
| Solubility of Sodium Percarbonate in Water (number of parts by weight per 100 parts by weight of water) | 15 |

*RATIO of the concentration in weight percent of $H_2O_2$ present in the hydrophilic bleaching agent particles to the concentration in weight percent of $H_2O_2$ present in the overall composition
[1]Sodium Percarbonate, Catalog number A16045 from Alfa Aesar, Ward Hill, MA. Solubility in water of 150 grams per liter (15 parts per 100 parts of water) - information from Wikipedia dated May 21 2018. Sieved through USA Standard Testing Sieve Number 40 with 425 micron opening.
[2]G2218 Grade from Sonneborn, LLC., Parsippany, NJ Comparative Example II Comparative example II is a commercially available Crest Whitestrips tooth whitening strip product with 5.25% $H_2O_2$ (from Procter & Gamble, Cincinnati, Ohio, USA). This is an aqueous gel containing 5.25% hydrogen peroxide ($H_2O_2$); and since it is an aqueous gel, the ratio of the concentration in weight percent of $H_2O_2$ present in the aqueous phase to the concentration in weight percent of $H_2O_2$ present in the overall composition is 1.

All examples were performed at room temperature (RT) and atmospheric pressure unless stated otherwise.

Ex-Vivo Procedure to Measure Bleaching Efficacy

1. Cut a circular disc (7.5 to 7.8 mm diameter×1.2 to 1.3 mm thickness) out of the front surface of a human incisor tooth. Leave the facial surface intact and flatten the lingual surface that has been cut out of the tooth. Soak the tooth-disc in 15 to 20 ml of water that meets USP specification in a glass vial for at least 24 hours. Repeat this for a total of 12 teeth. Measure the baseline L* and b* of the 24 tooth-discs using a hand-held spectrophotometer Konica Minolta 700d on three separate days and average the values across all three days.

2. Treat the group of 12 tooth-discs with the composition to be assessed. Specifically, cut circular discs of about 19.1 mm diameter from the same the polyethylene strip specified in the Clinical protocol. Apply about 0.05 gram of the composition in a circular disc of about 9.5 mm diameter to this polyethylene disc. Take the tooth-disc out of the water and place the composition and polyethylene disc on the facial surface of the tooth-disc while it is still wet such that the composition is sandwiched between the tooth-disc and polyethylene disc. Briefly apply slight pressure to the polyethylene disc to simulate the strip being positioned on the teeth. Place this sandwich in an oven set at about 34 C (to simulate the conditions of the facial surface of maxillary anterior teeth) for about 60 minutes.

3. If the multi-phase oral composition is used with electromagnetic radiation:
   After 50 minutes of treatment with the multi-phase oral composition, the electromagnetic radiation is applied toward the facial surface of the tooth-disc for 10 minutes.
   The electromagnetic radiation is directed toward the facial surface of the tooth-disc through the strip and through the multi-phase oral composition.

The electromagnetic radiation is delivered via a fiber-optic cable (model number M71L01 from Thorlabs, Newton, N.J., USA) connected to a high power LED with a peak intensity wavelength of 455 nm (model number M455F1 from Thorlabs, Newton, N.J., USA). The LED is run at 1000 mA using an LED Driver (model number DC2100, or DC4104 paired with DC4100-HUB from Thorlabs, Newton, N.J., USA). The exit end of the fiber-optic cable is mounted to help position the electromagnetic radiation reproducibly against the outer surface of the strip. The exit end of the fiber-optic cable is about 7 mm away from the tooth surface. The intensity of the electromagnetic radiation from 400 nm to 500 nm measured at the central axis of the cone of electromagnetic radiation at this distance needs to be from about 175 mW/cm$^2$ to about 225 mW/cm$^2$ as measured by the method disclosed herein.

This radiation is applied for about 10 minutes per tooth-disc.

4. Once 60 minutes of the treatment with the multi-phase oral composition is completed, the polyethylene disc is removed, and the residual composition is removed from the tooth-disc using a paper-towel and water.
5. After each treatment, soak the tooth-disc in 15 to 20 ml of water that meets USP specification in a glass vial for at least about 24 hours.
6. Finally, measure the post-treatment b*. This is done on three separate days and averaged across all three days.
7. Calculate the mean change in yellowness from baseline (Δb*).

Bleaching Efficacy

The bleaching efficacy of Example I-III and Comparative Example I delivered on a strip and used with an electromagnetic radiation source and measured according to the ex-vivo procedure specified herein are listed in TABLE 3.

TABLE 3

Bleaching Efficacy

|  | Ex. I | Ex. II | Ex. III | Comp. Ex. I |
| --- | --- | --- | --- | --- |
| % H$_2$O$_2$ | 3 | 3 | 3 | 3 |
| Hydrophilic Particle | Urea Peroxide | PVP Peroxide | PVP Peroxide (combined with Sodium Bicarbonate) | Sodium Percarbonate |
| Particle Solubility in H$_2$O | 80 | >40 | >40 | 15 |
| Hydrophobic Phase | Petrolatum | Petrolatum | Petrolatum Mineral Oil | Petrolatum |
| −Δb* | −3.11 | −2.57 | −5.07 | −0.84 |

TABLE 3 shows that Example I delivered a larger reduction in yellowness (−Δb*) Vs. Comparative Example I. These results clearly demonstrate the surprisingly high efficacy of Example I (made with Urea peroxide) Vs. Comparative Example I (made with Sodium percarbonate) even though both compositions had the same level of H$_2$O$_2$ (3%).

Specifically, these results clearly demonstrate the surprisingly high efficacy of a composition (Example I) made with hydrophilic bleaching agent particles (urea peroxide) that has a solubility of 80 parts by weight in 100 parts by weight of water Vs. a composition (Comparative Example I) made with hydrophilic bleaching agent particles (sodium percarbonate) that that has a solubility of only 15 parts by weight in 100 parts by weight of water, even though both compositions had the same level of H$_2$O$_2$ (3%). These results clearly demonstrate the surprisingly large impact of the solubility of the hydrophilic bleaching agent particles on bleaching efficacy.

TABLE 3 also shows that Example II [made with hydrophilic bleaching agent particles (Complex of hydrogen peroxide and polyvinylpyrrolidone polymer) that has a solubility >40 parts by weight in 100 parts by weight of water] delivered a surprisingly high reduction in yellowness (−Δb*) of 2.57 while Comparative Example I [made with hydrophilic bleaching agent particles (sodium percarbonate) that that has a solubility of only 15 parts by weight in 100 parts by weight of water] delivered a reduction in yellowness (−Δb*) of only 0.84 even though both compositions had the same level of H$_2$O$_2$ (3%). These results clearly demonstrate the surprisingly large impact of the solubility of the hydrophilic bleaching agent particles on bleaching efficacy.

TABLE 3 shows that Example III delivered a larger reduction in yellowness (−Δb*) Vs. Example II. These results clearly demonstrate the surprisingly high efficacy of Example III (made with Complex of hydrogen peroxide and polyvinylpyrrolidone polymer, combined with Sodium bicarbonate) Vs. Example II (made with Complex of hydrogen peroxide and polyvinylpyrrolidone polymer, but no Sodium bicarbonate) even though both compositions had the same level of H$_2$O$_2$ (3%).

Specifically, these results clearly demonstrate the surprisingly high efficacy of a composition (Example III) made with two or more oral care active agents that are normally incompatible with each other combined in the same composition Vs. a composition (Example II) made with only one oral care active agent. These results also clearly demonstrate the surprisingly large impact sodium bicarbonate has on bleaching efficacy when combined with hydrophilic bleaching agent particles.

Clinical Bleaching Efficacy of Example II and Comparative Example II

The bleaching efficacy of Example II was measured according to the clinical protocol specified herein. Specifically, this was a single-center clinical study conducted on adults who had never had a professional, over-the-counter or investigational tooth bleaching treatment. All participants were at least 18 years old, had all four measurable maxillary incisors, and had no self-reported tooth sensitivity.

Example II (20 participants, mean L* of 72.7 and mean b* of 15.4

The maxillary anterior teeth of the participants were treated with the oral composition for 60 minutes once daily using a strip of polyethylene as a delivery carrier. The polyethylene strips were 66 mm×15 mm in size and 0.0178 mm thick. 0.6 grams to 0.8 grams of the oral compositions were applied across each strip of polyethylene prior to applying to the maxillary anterior teeth.

Distribution of the maxillary strips and all applications were supervised by a clinical site staff. For each treatment, participants wore a strip with the oral composition for a total of 60 minutes. After 50 minutes of each strip wear, a trained hygienist applied electromagnetic radiation toward the facial surfaces of the maxillary anterior teeth for 10 minutes. The electromagnetic radiation was directed toward the teeth through the strip and through the oral composition. The electromagnetic radiation was delivered using the source of electromagnetic radiation described herein in the section titled "Clinical Protocol". The intensity of the electromagnetic radiation from 400 nm to 500 nm measured at the central axis of each cone of electromagnetic radiation exiting at the exit surface of the transparent window through which the electromagnetic radiation passes toward the maxillary anterior teeth was measured to be from about 175 mW/cm$^2$ to about 225 mW/cm$^2$, as measured by the procedure disclosed herein.

Digital images were collected at Baseline, and the day after the $1^{rd}$, $2^{nd}$ and $3^{rd}$ treatments.

The participants treated with Example II demonstrated a statistically significant (p<0.001), incremental reduction in yellowness ($-\Delta b^*$) at all tested time-points relative to Baseline; in addition, increase in lightness ($\Delta L^*$) was observed in this group the day after 2a and $3^{rd}$ treatments and (p<0.001).

The bleaching efficacy of a second comparative composition (Comparative Example II—Crest Whitestrips tooth whitening strip product with 5.25% $H_2O_2$) containing a final concentration of 5.25% $H_2O_2$ in an aqueous gel was measured in a clinical study. Specifically, the study for Comparative Example II was a controlled, single-center clinical trial. The target population was adult participants with no previous history of tooth whitening. Participants were treated with the above comparative aqueous gel with 5.25% $H_2O_2$ (Comparative Example II) delivered on a strip of polyethylene. The group (20 participants, mean L* of 72.8 and mean b* of 16.4) wore the strip for 60 minutes once daily for 14 days.

Digital images were obtained at Baseline, and the day after the $7^{th}$ and $14^{th}$ treatments. The results of the group who wore the Comparative Example II (aqueous gel with 5.25% $H_2O_2$) delivered on a strip for 60 minutes (same length of time as Example II in the clinical described previously) are shown in TABLE 4.

TABLE 4

Clinical Bleaching Efficacy

| Mean change in yellowness from baseline ($\Delta b^*$) | Example II (composition of invention containing about 3% $H_2O_2$) (delivered on a strip for 60 minutes, and used with an electromagnetic radiation source described herein in the section titled "Clinical Protocol") | Comparative Example II (aqueous gel containing about 5.25% $H_2O_2$) (delivered on a strip for 60 minutes) |
| --- | --- | --- |
| After 1 treatment (Day 2) | −1.14 | — |
| After 2 treatments (Day 3) | −1.73 | — |
| After 3 treatments (Day 4) | −2.61 | — |
| After 7 treatments (Day 8) | — | −0.985 |
| After 14 treatments (Day 15) | — | −1.43 |

After 7 treatments, the comparative Example II (aqueous gel with 5.25% $H_2O_2$, delivered on a strip for 60 minutes) produced a mean change in yellowness of −0.985 while Example II (also delivered on a strip, and used with an electromagnetic radiation source) delivered a mean change in yellowness of −1.14 after just 1 treatment even though it had a lower concentration of $H_2O_2$ vs. the aqueous gel (3% $H_2O_2$ Vs. 5.25% $H_2O_2$) used in Comparative Example II. Similarly, after 14 treatments, the comparative Example II produced a mean change in yellowness of −1.43 while Example II delivered a mean change in yellowness of −1.73 after just 2 treatments even though it had a lower concentration of $H_2O_2$ Vs. the aqueous gel (3% $H_2O_2$ vs. 5.25% $H_2O_2$). These results also clearly demonstrate the surprisingly high efficacy of Example II (delivered on a strip and used with an electromagnetic radiation source as disclosed herein) even though it has a lower concentration of $H_2O_2$ Vs. the comparative aqueous gel (3% $H_2O_2$ Vs. 5.25% $H_2O_2$) used in Comparative Example II.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-phase oral care composition comprising:
   a) solid hydrophilic bleaching agent particles, wherein at least 20 parts by weight of the solid hydrophilic bleaching agent particles are soluble in 100 parts, by weight of water; and
   b) at least about 60%, by weight of the multi-phase oral care composition, of hydrophobic phase.

2. The multi-phase oral care composition of claim 1, wherein at least 50 parts by weight of the hydrophilic bleaching agent particles are soluble in 100 parts by weight of water.

3. The multi-phase oral care composition of claim 2, wherein the hydrophilic bleaching agent particles comprise hydrogen peroxide adduct.

4. The multi-phase oral care composition of claim 3, wherein the hydrogen peroxide adduct comprises urea peroxide, polyvinyl pyrrolidone complexed with peroxide, or combinations thereof.

5. The multi-phase oral care composition of claim 1, wherein the hydrophilic bleaching agent particle swells by at least about 50% upon contact with water.

6. The multi-phase oral care composition of claim 1, wherein the hydrophilic bleaching agent particle is insoluble in the hydrophobic phase and the hydrophobic phase is insoluble in water.

7. The multi-phase oral care composition of claim 1, wherein the multi-phase oral care composition has a cone penetration consistency value of from about 25 to about 300.

8. The multi-phase oral care composition of claim 1, wherein the hydrophobic phase has a cone penetration consistency value of from about 50 to about 250.

9. The multi-phase oral care composition of claim 1, wherein the multi-phase oral care composition has a cone penetration consistency value of from about 50 to about 250.

10. The multi-phase oral care composition of claim 1, wherein the hydrophobic phase comprises mineral oil thickened with wax, mineral oil thickened with polyethylene, petrolatum, or combinations thereof.

11. The multi-phase oral care composition of claim 1, wherein the multi-phase oral care composition comprises an additional oral care agent.

12. The multi-phase oral care composition of claim 1, wherein the additional oral care agent comprises stannous fluoride, stannous chloride, or combinations thereof.

13. The multi-phase oral care composition of claim 1, wherein the hydrophobic phase comprises petrolatum.

14. The multi-phase oral care composition of claim 13, wherein the solid hydrophilic bleaching agent particles comprise urea peroxide.

15. The multi-phase oral care composition of claim 13, wherein the solid hydrophilic bleaching agent particles comprise polyvinyl pyrrolidone complexed with peroxide.

16. The multi-phase oral care composition of claim 15, wherein the polyvinyl pyrrolidone comprises crosslinked polyvinyl pyrrolidone.

17. The multi-phase oral care composition of claim 1, wherein the hydrophobic phase is petrolatum.

18. The multi-phase oral care composition of claim 17, wherein the solid hydrophilic bleaching agent particles comprise urea peroxide.

19. The multi-phase oral care composition of claim 17, wherein the solid hydrophilic bleaching agent particles comprise polyvinyl pyrrolidone complexed with peroxide.

20. The multi-phase oral care composition of claim 19, wherein the polyvinyl pyrrolidone comprises crosslinked polyvinyl pyrrolidone.

21. The multi-phase oral care composition of claim 1, wherein the multi-phase oral care composition is a semi-solid dispersion.

22. The multi-phase oral care composition of claim 21, wherein the solid hydrophilic bleaching agent particles comprise urea peroxide.

23. The multi-phase oral care composition of claim 21, wherein the solid hydrophilic bleaching agent particles comprise polyvinyl pyrrolidone complexed with peroxide.

24. The multi-phase oral care composition of claim 23, wherein the polyvinyl pyrrolidone comprises crosslinked polyvinyl pyrrolidone.

25. The multi-phase oral care composition of claim 1, wherein the multi-phase oral care composition comprises oral care active agent.

26. The multi-phase oral care composition of claim 25, wherein the oral care active agent comprises an anticalculus agent, a fluoride ion source, an antimicrobial agent, a remineralization agent, a dentinal desensitizing agent, an anesthetic agent, an antifungal agent, an anti-inflammatory agent, a selective H-2 antagonist, an anticaries agent, a nutrient, erythritol, a probiotic, resolvin, tranexamic acid, retinol, an amino acid, niacinamide, human growth factors, or mixtures thereof.

27. A kit for whitening teeth comprising:
a) the multi-phase oral care composition of claim 1; and
b) an electromagnetic radiation source capable of directing electromagnetic radiation with one or more wavelengths in the range from about 200 nm to about 1700 nm towards at least one tooth.

28. The kit for whitening teeth according to claim 27, wherein the electromagnetic radiation source is capable of emitting electromagnetic radiation with a wavelength in the range from about 400 nm to about 500 nm and an intensity in the range from about 175 mW/cm$^2$ to about 225 mW/cm$^2$.

29. A kit for whitening teeth comprising:
a) the multi-phase oral care composition of claim 1; and
b) a delivery carrier.

30. The kit of claim 29, wherein the delivery carrier comprises a strip, a film of material, a dental tray, a sponge material, an applicator, or mixtures thereof.

31. A method for whitening teeth comprising:
a) applying the multi-phase oral care composition of claim 1 to a delivery carrier; and
b) contacting said multi-phase oral care composition combined with the delivery carrier with at least one tooth surface.

32. The method of claim 31, wherein the method further comprises:
c) directing electromagnetic radiation with one or more wavelengths in the range from about 200 nm to about 1700 nm towards the at least one tooth.

* * * * *